(12) United States Patent
Pilz et al.

(10) Patent No.: US 9,295,626 B2
(45) Date of Patent: Mar. 29, 2016

(54) COMPOSITIONS COMPRISING ISOSORBIDE MONOESTER AND N-HYDROXYPYRIDONES

(75) Inventors: Maurice Frederic Pilz, Frankfurt am Main (DE); Peter Klug, Grobostheim (DE); Franz-Xaver Scherl, Burgkirchen (DE); Joerg Grohmann, Niedernhausen (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 14/237,024

(22) PCT Filed: Jul. 31, 2012

(86) PCT No.: PCT/EP2012/003248
§ 371 (c)(1),
(2), (4) Date: Jul. 16, 2014

(87) PCT Pub. No.: WO2013/017259
PCT Pub. Date: Feb. 7, 2013

(65) Prior Publication Data
US 2014/0343171 A1    Nov. 20, 2014

(30) Foreign Application Priority Data
Aug. 4, 2011 (DE) .......................... 10 2011 109 488

(51) Int. Cl.
| | | |
|---|---|---|
| A61K 8/49 | (2006.01) |
| A01N 43/90 | (2006.01) |
| A61Q 1/14 | (2006.01) |
| A61Q 5/00 | (2006.01) |
| A61Q 5/02 | (2006.01) |
| A61Q 5/06 | (2006.01) |
| A61Q 15/00 | (2006.01) |
| A61Q 17/04 | (2006.01) |
| A61Q 19/00 | (2006.01) |
| A61Q 19/02 | (2006.01) |
| A61Q 19/04 | (2006.01) |
| A61Q 19/08 | (2006.01) |
| A61Q 19/10 | (2006.01) |

(52) U.S. Cl.
CPC .............. *A61K 8/4973* (2013.01); *A01N 43/90* (2013.01); *A61K 8/4926* (2013.01); *A61Q 1/14* (2013.01); *A61Q 5/006* (2013.01); *A61Q 5/02* (2013.01); *A61Q 5/06* (2013.01); *A61Q 15/00* (2013.01); *A61Q 17/04* (2013.01); *A61Q 19/00* (2013.01); *A61Q 19/02* (2013.01); *A61Q 19/04* (2013.01); *A61Q 19/08* (2013.01); *A61Q 19/10* (2013.01); *A61K 2300/00* (2013.01)

(58) Field of Classification Search
CPC .................................................. A61K 8/4973
USPC ................................................ 514/470, 875
See application file for complete search history.

(56) References Cited

U.S. PATENT DOCUMENTS

| | | |
|---|---|---|
| 3,331,742 A | 7/1967 | Babayan |
| 4,637,930 A | 1/1987 | Konno et al. |
| 4,711,775 A | 12/1987 | Dittmar et al. |
| 4,847,088 A | 7/1989 | Blank |
| 6,413,529 B1 | 7/2002 | Beerse et al. |
| 8,642,525 B2 | 2/2014 | Herrwerth et al. |
| 2005/0222276 A1 | 10/2005 | Schmaus et al. |
| 2007/0178144 A1 | 8/2007 | Hameyer et al. |
| 2008/0142023 A1 | 6/2008 | Schmid |
| 2008/0312195 A1 | 12/2008 | Simsch et al. |
| 2010/0113664 A1 | 5/2010 | Bradshaw et al. |
| 2011/0104085 A1 | 5/2011 | Klug et al. |
| 2011/0117036 A1 | 5/2011 | Chaudhuri et al. |
| 2012/0100085 A1 | 4/2012 | Klug et al. |
| 2012/0101135 A1 | 4/2012 | Klug et al. |
| 2012/0116101 A1 | 5/2012 | Fuertes et al. |

(Continued)

FOREIGN PATENT DOCUMENTS

| | | |
|---|---|---|
| CA | 1231046 | 1/1988 |
| DE | 3328372 | 3/1984 |

(Continued)

OTHER PUBLICATIONS

English-Translation of International Preliminary Report on Patentability for PCT/EP2012/003248 dated Feb. 4, 2014.
International Search Report for PCT/EP2012/003248 dated Oct. 18, 2012.
Frieder W. Lichtenthaler, "Carbohydrates, Chapter 9: Carbohydrates as Organic Raw Materials," Ullmann's Encyclopedia of Industrial Chemistry, vol. 6, pp. 262-273, Jan. 1, 2003.
Dubini Francesco et al., "In Vitro Antimycotic Activity and Nail Permeation Models of a Prioctone Olamine (Octopirox) Containing Transungual Water Soluble Technology," Arzneimittel Forschung. Drug Research, ECV Editio Cantor Verlag, vol. 55 No. 8, pp. 478-483, Jan. 1, 2005.

(Continued)

*Primary Examiner* — Taofiq A Solola
(74) *Attorney, Agent, or Firm* — Tod A. Waldrop

(57) ABSTRACT

What are described are compositions comprising
a) one or more compounds of the formula (I)

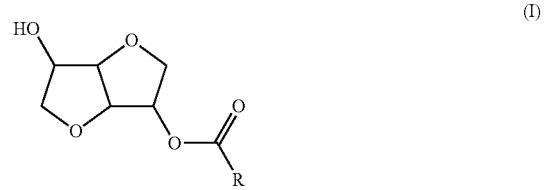

(I)

in which
R is a straight-chain or branched saturated alkyl group having 5 to 11 carbon atoms or a straight-chain or branched mono- or polyunsaturated alkenyl group having 5 to 11 carbon atoms, and
b) one or more substances selected from the group consisting of hydroxypyridones and their salts.
The compositions are distinguished in particular by an advantageous antimicrobial activity.

10 Claims, No Drawings

(56) References Cited

U.S. PATENT DOCUMENTS

| | | |
|---|---|---|
| 2014/0308224 A1 | 10/2014 | Pilz et al. |
| 2014/0315996 A1 | 10/2014 | Pilz et al. |
| 2014/0322151 A1 | 10/2014 | Fricke et al. |
| 2014/0323564 A1 | 10/2014 | Pilz et al. |
| 2014/0323592 A1 | 10/2014 | Pilz et al. |
| 2014/0329870 A1 | 11/2014 | Pilz et al. |
| 2014/0348763 A1 | 11/2014 | Pilz et al. |
| 2014/0369943 A1 | 12/2014 | Pilz et al. |
| 2015/0030553 A1 | 1/2015 | Pilz et al. |

FOREIGN PATENT DOCUMENTS

| | | |
|---|---|---|
| DE | 2234009 | 12/1987 |
| DE | 10 2009 022 445 A1 | 12/2009 |
| DE | 10 2009 022 444 A1 | 1/2010 |
| EP | 1813251 | 8/2007 |
| EP | 1972330 | 9/2008 |
| EP | 2239315 | 10/2010 |
| JP | 59-175408 | 10/1984 |
| JP | H01313408 | 12/1989 |
| JP | H03168075 | 7/1991 |
| JP | 8173787 A | 7/1996 |
| JP | 8187070 A | 7/1996 |
| JP | H09291016 | 11/1997 |
| JP | 2002541181 | 12/2002 |
| JP | 2003238396 | 8/2003 |
| JP | 2007203288 | 8/2007 |
| WO | WO 2006103338 | 10/2006 |
| WO | WO 2008155159 | 12/2008 |
| WO | 2010108738 A2 | 9/2010 |
| WO | 2010136121 A2 | 12/2010 |

OTHER PUBLICATIONS

Peter Stoss et al., "Regioselektive Acylierung von 1, 4:3, 6-Dianhydro-D-glucit," Synthesis, vol. 1987, No. 02, pp. 174-176, Jan. 1, 1987.
English-language Abstract of JP 8173787.
English-language Abstract of JP 8187070.
International Preliminary Report on Patentability for PCT/EP2010/002918, Dec. 2, 2011.
International Preliminary Report on Patentability for PCT/EP2010/002919, dated Feb. 28, 2012.
International Search Report for PCT/EP2010/002918 mail date Jun. 30, 2011.
Bach M. et al. Konservierungsmittel Und Ihre Praktische Anwendung in Kosmetischen Produkten, Sofw-Journal Seifen, Oele, Fette, Wachse, Verlag Fur Chemische Industrie, Angsburg, DE, vol. 116, No. 9, Jun. 13, 1990. pp. 942-7694, XP000134744.
Christian W. Klampfl et al., "Quantitative determination of UV filters in sunscreen lotions using microemulsion electrokinetic chromatography," J. Sep. Sci. Sep. 26, 2003, 1259-1262.
Database CA (Online) Chemical Abstracts Service, Feb. 24, 1985, "Cosmetics Containing Isosrbide Fatty Acid Diesters," Database Accession No. 1985:67233. English-language abstract of JP 59-175408.
Database CA (Online), Chemical Abstracts Service, Columbus, Ohio (May 12, 1984), Miura Takeshi, Ishida Katsuo; "Rinsing assistants", XP002643079. English abstract of JP 51056809.
Database CA (Online), Chemical Abstracts Service, Columbus, Ohio (May 12, 1984), Miura Takeshi, Ishida Katsuo; "Rinsing assistants", XP002643080. English abstract of JP 51068608.
Database CA (Online), Chemical Abstracts Service, Columbus, Ohio (Sep. 29, 2000), Fukushima Noriko; "Water-soluble rinses for dishwashers", XP002643077.
Database CA (Online), Chemical Abstracts Service, Columbus, Ohio (Sep. 18, 2003), Miura Takeshi, et al.; "Coenzyme Q10-containing emulsions, and manufacture thereof", XP002643081. English abstract of JP 2003238396.
Database CA (Online), Chemical Abstracts Service, Columbus, Ohio (Aug. 14, 2008), Mori Toshiki; "Transparent cleaners comprising nonionic surfactants", XP002643078.
Database GNPD (Online), (Feb. 1999), Mintel; "Verzorgende Shampoo-Lang Harr", XP002662186.
English Abstract for JPH03168075, Jul. 19, 1991.
English Abstract for JPH09291016, Nov. 11, 1997.
English-translation of International Preliminary Report on Patentability for PCT/EP2012/003244 dated Feb. 4, 2014.
English-translation of International Preliminary Report on Patentability for PCT/EP2012/003245 dated Feb. 21, 2014.
English-translation of International Preliminary Report on Patentability for PCT/EP2012/003246 dated Feb. 4, 2014.
English-Translation of International Preliminary Report on Patentability for PCT/EP2012/003247 dated Mar. 24, 2014.
English-translation of International Preliminary Report on Patentability for PCT/EP2012/003252 dated Feb. 4, 2014.
English-translation of International Preliminary Report on Patentability for PCT/EP2012/003253 dated Feb. 4, 2014.
F.C. Kull et al., Applied Microbiology 1961, 9, 538.
Giacometti, J. et al., "Process for Preparing Nonionic Surfactant Sorbitan Fatty Acid Esters with and without Previous Sorbitol Cyclization", J. of Agricultural and Food Chemistry, American Chemical Society, vol. 44, Jan. 1, 1996, pp. 3950-3954.
International Search Report for PCT/EP2010/002919 mail date Nov. 15, 2011.
International Search Report for PCT/EP2012/003244 dated Oct. 18, 2012.
International Search Report for PCT/EP2012/003245 dated Oct. 5, 2012.
International Search Report for PCT/EP2012/003246 dated Oct. 18, 2012.
International Search Report for PCT/EP2012/003247 dated Oct. 18, 2012.
International Search Report for PCT/EP2012/003249 dated Oct. 5, 2012.
International Search Report for PCT/EP2012/003250 dated Oct. 5, 2012.
International Search Report for PCT/EP2012/003251 dated Oct. 10, 2012.
International Search Report for PCT/EP2012/003252 dated Oct. 8, 2012.
International Search Report for PCT/EP2012/003253 dated Oct. 8, 2012.
International Search Report for PCT/EP2012/004827 dated Jan. 7, 2014.
Seal, Kenneth J. et al., "Benzisothiazolinone and Methylisothiazolinone. New Preservative System," Cosmetic Technology, CEC, vol. 5, No. 1, pp. 47-52, Jan. 1, 2002.
Translation of International Preliminary Report on Patentability for PCT/EP2012/003249 dated Feb. 4, 2014.
Translation of International Preliminary Report on Patentability for PCT/EP2012/003250 dated Feb. 4, 2014.
Translation of International Preliminary Report on Patentability for PCT/EP2012/003251 dated Feb. 4, 2014.
USPTO Ex Parte Quayle Action for U.S. Appl. No. 14/237,071, dated Jun. 24, 2015.
USPTO Final Rejection for U.S. Appl. No. 13/321,178, dated Dec. 4, 2013.
USPTO Final Rejection for U.S. Appl. No. 13/321,199, dated Mar. 19, 2015.
USPTO Final Rejection for U.S. Appl. No. 13/321,199, dated Dec. 24, 2013.
USPTO Final Rejection for U.S. Appl. No. 14/237,042, dated Jul. 8, 2015.
USPTO Final Rejection for U.S. Appl. No. 14/237,053, dated Sep. 8, 2015.
USPTO Non-Final Rejection for U.S. Appl. No. 13/321,178, dated Apr. 30, 2013.
USPTO Non-Final Rejection for U.S. Appl. No. 13/321,178, dated May 6, 2014.
USPTO Non-Final Rejection for U.S. Appl. No. 13/321,199, dated Apr. 22, 2013.
USPTO Non-Final Rejection for U.S. Appl. No. 13/321,199, dated Aug. 18, 2015.

(56) References Cited

OTHER PUBLICATIONS

USPTO Non-Final Rejection for U.S. Appl. No. 13/321,199, dated Sep. 5, 2014.
USPTO Non-Final Rejection for U.S. Appl. No. 14/237,039, dated Aug. 14, 2015.
USPTO Non-Final Rejection for U.S. Appl. No. 14/237,042, dated Dec. 17, 2014.
USPTO Non-Final Rejection for U.S. Appl. No. 14/237,053, dated May 7, 2015.
USPTO Non-Final Rejection for U.S. Appl. No. 14/237,076, dated Sep. 9, 2015.
USPTO Requirement for Restriction/Election for U.S. Appl. No. 13/321,178, dated Jan. 10, 2013.
USPTO Requirement for Restriction/Election for U.S. Appl. No. 13/321,199, dated Nov. 7, 2012.
USPTO Requirement for Restriction/Election for U.S. Appl. No. 14/237,027, dated Jan. 28, 2015.
USPTO Requirement for Restriction/Election for U.S. Appl. No. 14/237,039, dated Aug. 14, 2015.
USPTO Requirement for Restriction/Election for U.S. Appl. No. 14/237,071, dated Jan. 28, 2015.
Sorbitan Caprylate—the Preservative Boosting, Multifunctional Ingredient, Frederic Pilz, Cosmetic Science Technology, 2011, pp. 131-134.
A welcome side effect: How Velsan® SC (Sorbitan Caprylate) helps to reduce the concentration of classical preservatives, Fredric Pilz, et al., Household and Personal Care Today, Mar. 2010, pp. 22-24.
Velsan SC: Caprilato de sorbitán—Ingrediente multifuncional, conservante, hidrótropo y agente co-emulsionante, Fredric Pilz, et al., NCP 322, Nov.-Dec. 2011, pp. 15-19.
A preservative-free solution, Fredric Pilz, SPC, Oct. 2011.
Presentation by Fredric Pilz, at In-Cosmetics 2010 Paris, Apr. 5, 2010.
Presentation by Fredric Pilz, at SCS Formulate, Nov. 10, 2010.
Presentation by Fredric Pilz, at HPCI Koferenz—Asien, Dec. 17, 2010.
Presentation by Fredric Pilz, at In-Cosmetics 2011 Milano, Mar. 31, 2011.
Presentation by Fredric Pilz, at HPCI Koferenz—Turkey, Jun. 2, 2011.

COMPOSITIONS COMPRISING ISOSORBIDE MONOESTER AND N-HYDROXYPYRIDONES

The present invention relates to compositions comprising isosorbide monoesters and one or more substances selected from the group consisting of hydroxypyridones and their salts. These compositions may be, for example, cosmetic, dermatological or pharmaceutical compositions, or else compositions which may be used for producing cosmetic, dermatological or pharmaceutical compositions. The present invention also relates to the use of compositions comprising isosorbide monoesters and one or more substances selected from the group consisting of hydroxypyridones and their salts for preserving cosmetic, dermatological or pharmaceutical compositions.

In industry, preservatives are used to protect products such as, for example, cosmetic, dermatological or pharmaceutical compositions against microbial attack. Numerous preservatives which can be used for this purpose are known. It is known, for example, that hydroxypyridones such as the monoethanolamine salt of 4-methyl-6-(2,4,4-trimethylpentyl)-1-hydroxy-2-pyridone (Octopirox®, Clariant) can be used to this end.

However, many preservatives have the disadvantage that, frequently, their preparation is expensive and based on synthetic raw materials. In addition, their preserving action frequently requires improvement, with high use concentrations being required for satisfactory preservation.

Accordingly, it was an object of the present invention to provide compositions having an advantageous preservation performance or advantageous stability to microbial attack and which are furthermore distinguished by the advantage that they are based at least in part on renewable raw materials.

Surprisingly, it has now been found that this object is achieved by compositions comprising a) one or more compounds of the formula (I)

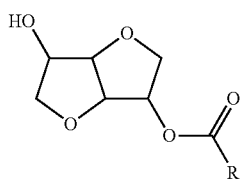

in which
R is a straight-chain or branched saturated alkyl group having 5 to 11, preferably 7 to 9 and particularly preferably 7 carbon atoms or a straight-chain or branched mono- or polyunsaturated alkenyl group having 5 to 11, preferably 7 to 9 and particularly preferably 7 carbon atoms, and
b) one or more substances selected from the group consisting of hydroxypyridones and their salts.

Accordingly, the invention provides compositions comprising
a) one or more compounds of the formula (I)

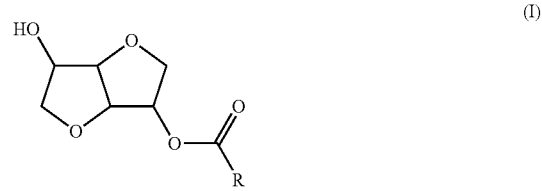

in which
R is a straight-chain or branched saturated alkyl group having 5 to 11, preferably 7 to 9 and particularly preferably 7 carbon atoms or a straight-chain or branched mono- or polyunsaturated alkenyl group having 5 to 11, preferably 7 to 9 and particularly preferably 7 carbon atoms, and
b) one or more substances selected from the group consisting of hydroxypyridones and their salts.

The compositions according to the invention have very good preservation performance or very good stability to microbial attack and owing to the presence of the compounds of the formula (I) are also based on renewable raw materials. Since the compounds of the formula (I) surprisingly increase the preservative effect of substances selected from the group consisting of hydroxypyridones and their salts synergistically, the use concentration of the hydroxypyridones and/or their salts based on synthetic raw materials can be reduced significantly, while maintaining an excellent antimicrobial effect of the compositions according to the invention or excellent stability of the compositions according to the invention to microbial attack.

Compared to the use of organic acids as preservatives, the compositions according to the invention also have the advantage of an activity or stability to microbial attack over a wider pH range. Whereas organic acids frequently only have good activity in the pH range from 3.5 to 6, the compositions according to the invention can also be employed advantageously at higher pH.

Compositions, for example cosmetic, dermatological or pharmaceutical compositions, comprising esters based on renewable raw materials are already known.

WO 2010/108738 A2 (Evonik) describes formulations which are used to clean and care for human or animal body parts and comprise sorbitancarboxylic esters, where the carboxylic acid portion of the sorbitancarboxylic ester is derived from a carboxylic acid containing 6 to 10 carbon atoms and the sorbitancarboxylic esters have a hydroxyl value of more than 350, and the use of the sorbitancarboxylic esters mentioned as viscosity regulators, care ingredient, foam booster or solubilizer in cleaning or care formulations.

DE 10 2009 022 444 (Clariant) describes liquid compositions comprising sorbitan monocaprylate and antimicrobially active compounds such as, for example, pyridones and their salts selected from 1-hydroxy-4-methyl-6-(2,4,4-trimethylpentyl)-2-pyridone and its monoethanolamine salt (piroctone olamine), and also their use for preserving cosmetic, dermatological or pharmaceutical products.

DE 10 2009 022 445 (Clariant) discloses liquid compositions comprising sorbitan monocaprylate and alcohol and their use for preserving cosmetic, dermatological or pharmaceutical products.

JP 8173787 (A) (Lion) describes a composition comprising a surfactant comprising a fatty ester of dehydrated sorbitol, and the use as oil-in-water emulsifier and as cleaner base. The compositions may comprise mono- or diesters of caprylic and/or caprinic acid with a polyol selected from the group consisting of 1,5-sorbitan, 1,4-sorbitan and isosorbide.

JP 8187070 (A) (Lion) discloses a mixture of fatty acid monoesters of $C_8$-$C_{18}$ fatty acids and at least one polyol selected from sorbitol, 1,5-sorbitan, 1,4-sorbitan and isosorbide and fatty acid diesters of these fatty acids and polyols in a weight ratio of monoester:diester of 33:7 to 9:1 as antimicrobially active compound against bacteria for food or beverages.

Compounds of components a) and b) of the compositions according to the invention are commercially available or can be produced by methods known to the person skilled in the art. For example, the compounds of the formula (I) can be prepared by esterification of isosorbide by customary methods known to the person skilled in the art, with both isosorbide for its part and also the acid component used for esterification once more being commercially available.

Preferably, the radical R in the one or more compounds of the formula (I) is a straight-chain saturated alkyl radical having 7 to 9 carbon atoms.

Particularly preferably, the radical R in the one or more compounds of the formula (I) is a straight-chain saturated alkyl radical having 7 carbon atoms.

Preferably, the one or more substances of component b) are selected from among compounds of the formula (II) and their salts

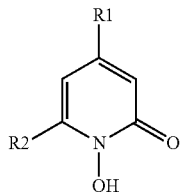

in which R1 is H or a $C_1$-$C_4$-alkyl radical and R2 is H, an unsubstituted or halogen-substituted branched or straight-chain $C_1$-$C_{20}$-alkyl radical, an unsubstituted or halogen-substituted $C_5$-$C_8$-cycloalkyl radical, an unsubstituted or halogen-substituted $C_6$-$C_{10}$-aryl radical or an unsubstituted or halogen-substituted branched or straight-chain $C_7$-$C_{20}$-aralkyl radical.

Preferably, the radicals R2 are not substituted by halogen.

In a preferred embodiment of the invention, the one or more compounds of component b) are present in the form of the acid (compounds of the formula (II)) or in the form of their alkali metal, alkaline earth metal or amine salts or their salts with polymeric counterions in the compositions according to the invention.

In the one or more compounds of formula (II) or their salts, R1 is preferably methyl and R2 is preferably cyclohexyl or 2,4,4-trimethylpentyl.

Particularly preferably, the compounds of the formula (II) are present in the form of their alkanol amine salts and especially preferably in the form of their monoethanolamine salts. Examples of such salts are mentioned in DE 2234009.

Particular preference is given to 4-methyl-6-(2,4,4-trimethylpentyl)-1-hydroxy-2-pyridone, the monoethanolamine salt of 4-methyl-6-(2,4,4-trimethylpentyl)-1-hydroxy-2-pyridone (Octopirox®, Clariant) and 4-methyl-6-(cyclohexyl)-1-hydroxy-2-pyridone and the monoethanolamine salt of 4-methyl-6-(cyclohexyl)-1-hydroxy-2-pyridone (Ciclopirox®, Sanofi-Aventis).

These substances can be obtained by processes known from the literature, compare, for example, the references mentioned in DE 2234009.

Most preferably, the compound of component b) is the monoethanolamine salt of 4-methyl-6-(2,4,4-trimethylpentyl)-1-hydroxy-2-pyridone.

Furthermore preferably, the radical R in the one or more compounds of the formula (I) is a straight-chain saturated alkyl radical having 7 carbon atoms, and the compound of component b) is the monoethanolamine salt of 4-methyl-6-(2,4,4-trimethylpentyl)-1-hydroxy-2-pyridone.

In a further preferred embodiment of the invention, the compositions according to the invention comprise
I) from 0.05 to 0.7, preferably from 0.1 to 0.7 and particularly preferably from 0.2 to 0.5 parts by weight of isosorbide and
II) from 0.1 to 1.0, preferably from 0.2 to 1.0 and particularly preferably from 0.4 to 0.8 parts by weight of isosorbide diester of the formula

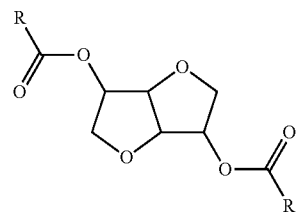

where R has the meaning given for formula (I) and where the isosorbide diester is preferably isosorbide dicaprylate, in each case based on 1.0 part by weight of the one or more compounds of the formula (I) and preferably based on 1.0 part by weight of isosorbide monocaprylate.

In an embodiment, which is in turn preferred, of this embodiment of the invention, the compositions according to the invention comprise either no carboxylic acid RCOOH or up to 0.1, preferably 0.001 to 0.05 and particularly preferably 0.002 to 0.01 parts by weight of carboxylic acid RCOOH, where R has the meaning given for formula (I) and where the carboxylic acid is preferably caprylic acid, based on 1.0 part by weight of the one or more compounds of the formula (I) and preferably based on 1.0 part by weight of isosorbide monocaprylate.

In a further preferred embodiment of the invention, the compositions according to the invention additionally comprise one or more sorbitan esters of sorbitan and carboxylic acids $R^aCOOH$, preferably selected from sorbitan esters from 1,4- and/or 1,5-sorbitan and carboxylic acids $R^aCOOH$ where $R^a$ is a straight-chain or branched saturated alkyl group having 5 to 11, preferably 7 to 9 and particularly preferably 7 carbon atoms or a straight-chain or branched mono- or polyunsaturated alkenyl group having 5 to 11, preferably 7 to 9 and particularly preferably 7 carbon atoms, and where the weight ratio of the one or more compounds of the formula (I) to the one or more sorbitan esters just mentioned is from 70:30 to 100:0, preferably from 80:20 to 100:0, particularly preferably from 90:10 to 100:0 and especially preferably from 95:5 to 100:0. The stated weight ratio of "100:0" means that in this preferred embodiment of the invention, the compositions according to the invention do not need to comprise any sorbitan ester.

From among the compositions according to the invention just mentioned, preference is given to those in which the one or more sorbitan esters of sorbitan and carboxylic acids R$^a$COOH are selected from sorbitan esters of sorbitan and caprylic acid and are preferably selected from sorbitan esters of 1,4- and/or 1,5-sorbitan and caprylic acid and the sorbitan ester is particularly preferably sorbitan monocaprylate.

In these compositions, the hydroxyl value of the mixture of the one or more compounds of the formula (I) and the one or more (if present) sorbitan esters of sorbitan and carboxylic acids R$^a$COOH is preferably smaller than or equal to 320, particularly preferably smaller than or equal to 285, especially preferably smaller than or equal to 245 and most preferably smaller than or equal to 225.

In a further preferred embodiment of the invention, the compositions according to the invention comprise, in addition to the one or more compounds of the formula (I), one or more compounds selected from the group consisting of sorbitol, sorbitol esters (sorbitol esters can be mono-, di-, tri-, tetra-, penta- and/or hexaesters), sorbitan, sorbitan esters (sorbitan esters can be mono-, di-, tri- and/or tetraesters), isosorbide, isosorbide diesters and carboxylic acids. "Sorbitan" can be, for example, 1,4- or 1,5-sorbitan. Both the carboxylic acids themselves and the carboxylic acids on which the acid components of the esters mentioned are based correspond to the formula RCOOH in which R has the meaning given for formula (I) and is preferably a straight-chain saturated alkyl radical having 7 carbon atoms, i.e. the carboxylic acid RCOOH is preferably caprylic acid. In the preferred embodiment of the invention described herein, the hydroxyl value of the mixture of the one or more compounds of the formula (I) and the one or more compounds selected from the group consisting of sorbitol, sorbitol esters, sorbitan, sorbitan esters, isosorbide, isosorbide diesters and carboxylic acids is smaller than or equal to 320, preferably smaller than or equal to 285, particularly preferably smaller than or equal to 245 and especially preferably smaller than or equal to 225.

In a further preferred embodiment of the invention, the compositions according to the invention do not comprise any compounds selected from sorbitol and sorbitol esters.

In a further preferred embodiment of the invention, the compositions according to the invention do not comprise any compounds selected from sorbitan and sorbitan esters.

In a preferred embodiment of the invention, the compositions according to the invention comprise the one or more compounds of component a) in amounts of from 10.0 to 99.5% by weight, preferably in amounts of from 20.0 to 90.0% by weight and particularly preferably in amounts of from 30.0 to 75.0% by weight and the one or more substances of component b) in amounts of from 0.5 to 50.0% by weight, preferably in amounts of from 1.0 to 30.0% by weight and particularly preferably in amounts of from 5.0 to 10.0% by weight, in each case based on the total weight of the composition.

The compositions according to the invention just mentioned, which comprise the compounds of component a) and the substances of component b) in relatively high amounts, may be, for example, compositions or "premixes" which can be used for producing cosmetic, dermatological or pharmaceutical compositions.

If these compositions or premixes according to the invention do comprise one or more compounds selected from the group consisting of sorbitol and sorbitol esters (where the carboxylic acid on which the acid component of these esters is based is preferably caprylic acid), these compounds together are preferably present in the compositions according to the invention in an amount smaller than or equal to 5.0% by weight, particularly preferably in an amount smaller than or equal to 3.0% by weight, especially preferably in an amount smaller than or equal to 1.0% by weight and most preferably in an amount smaller than or equal to 0.5% by weight, the stated % by weight in each case being based on the total weight of the finished composition or premix according to the invention.

If these compositions or premixes according to the invention do comprise one or more compounds selected from the group consisting of sorbitan and sorbitan esters (where the carboxylic acid on which the acid component of these esters is based is preferably caprylic acid), these compounds together are preferably present in the compositions according to the invention in an amount smaller than or equal to 20.0% by weight, particularly preferably in an amount smaller than or equal to 10.0% by weight, especially preferably in an amount smaller than or equal to 5.0% by weight and most preferably in an amount smaller than or equal to 1% by weight, the stated % by weight in each case being based on the total weight of the finished composition or premix according to the invention.

In a preferred embodiment of the invention, these compositions or premixes according to the invention comprise, in addition to the compounds of component a) and the substances of component b), one or more alcohols, the latter preferably being selected from the group consisting of propylene glycol, phenoxyethanol and benzyl alcohol, and are liquid at room temperature (25° C.). In a preferred embodiment of this embodiment of the invention, the alcohol is propylene glycol, in another preferred embodiment of this embodiment of the invention, the alcohol is phenoxyethanol and in a further preferred embodiment of this embodiment of the invention, the alcohol is benzyl alcohol.

In a further preferred embodiment of the invention, these compositions or premixes according to the invention consist of the compounds of component a) and the compounds of component b), where, however, in this preferred embodiment of the invention, depending on the preparation of the compounds of component a), additionally one or more compounds selected from the group consisting of sorbitol, sorbitol esters, sorbitan, sorbitan esters, isosorbide, isosorbide diesters and carboxylic acids RCOOH may be present. In this preferred embodiment of the invention, these compositions or premixes according to the invention can be solid at room temperature (25° C.) and they are preferably solid at room temperature (25° C.). Preferably, these compositions or premixes according to the invention comprise at least 50% by weight of the one or more compounds of component a), based on the total weight of these compositions or premixes according to the invention, without the one or more compounds of component b) being taken into account.

The pH of these compositions or premixes according to the invention, measured as a 5% by weight strength solution in ethanol/water (weight ratio ethanol:water 1:1) is preferably 4 to 9, particularly preferably 5 to 8 and especially preferably 5.5 to 7.5.

A further advantage of the compositions according to the invention and in particular the compositions or premixes according to the invention just mentioned is that, in addition to the very good preserving action, they also display an advantageous action as thickeners.

The hydroxyl value of a substance is to be understood as meaning the amount of KOH in mg equivalent to the amount of acetic acid bound during the acetylation of 1 g of substance.

Suitable determination methods for determining the hydroxyl value are, for example, DGF C-V 17 a (53), Ph. Eur. 2.5.3 Method A and DIN 53240.

In the context of the present invention, the hydroxyl values are determined analogously to DIN 53240-2. Here, the following procedure is adopted: 1 g, accurate to 0.1 mg, of the homogenized sample to be measured is weighed out. 20.00 ml of acetylation mixture (acetylation mixture: 50 ml of acetic anhydride are stirred into 1 l of pyridine) are added. The sample is dissolved completely in the acetylation mixture, if required with stirring and heating. 5 ml of catalyst solution (catalyst solution: 2 g of 4-dimethylaminopyridine are dissolved in 100 ml of pyridine) are added. The reaction vessel is closed and placed into the water bath, preheated to 55° C., for 10 minutes, with mixing. 10 ml of fully deionized water are then added to the reaction solution, the reaction vessel is closed again and the mixture is once more allowed to react in the water bath with shaking for 10 minutes. The sample is then cooled to room temperature (25° C.). 50 ml of 2-propanol and 2 drops of phenolphthalein are then added. This solution is titrated with aqueous sodium hydroxide solution (aqueous sodium hydroxide solution c=0.5 mol/l) (Va). Under identical conditions, but without any sample added, the efficacy of the acetylation mixture is determined (Vb).

From the aqueous sodium hydroxide solution consumed in the determination of the efficacy and the titration of the sample, the hydroxyl value (OHV) is calculated using the following formula:

$$OHV = \frac{(Vb - Va) \cdot c \cdot t \cdot M}{E}$$

OHV=hydroxyl value in mg KOH/g substance
Va=aqueous sodium hydroxide solution consumed in ml during the titration of the sample
Vb=aqueous sodium hydroxide solution consumed in ml during the titration of efficacy
c=molar concentration of the aqueous sodium hydroxide solution in mol/l
t=titer of the aqueous sodium hydroxide solution
M=molar mass of KOH=56.11 g/mol
E=sample weighed out in g
(Vb−Va) is the amount of aqueous sodium hydroxide solution used in ml, which is equivalent to the amount of acetic acid bound during the above-described acetylation of the sample to be measured.

Hereinbelow, the method just described for determining the hydroxyl value is referred to as "method OHV-A".

In a further preferred embodiment of the invention, the compositions according to the invention are cosmetic, dermatological or pharmaceutical compositions.

As already mentioned, the cosmetic, dermatological or pharmaceutical compositions according to the invention can be prepared from the premixes according to the invention. However, alternatively they can also be prepared by separate use of the one or more compounds of the formula (I) and the one or more substances of component b).

The cosmetic, dermatological or pharmaceutical compositions according to the invention comprise the one or more compounds of component a) preferably in amounts of from 0.01 to 10.0% by weight, particularly preferably in amounts of from 0.1 to 5.0% by weight and especially preferably in amounts of from 0.2 to 3.0% by weight and the one or more substances of component b) preferably in amounts of from 0.001 to 1.0% by weight, particularly preferably in amounts of from 0.01 to 0.8% by weight and especially preferably in amounts of from 0.1 to 0.5% by weight, in each case based on the total weight of the composition according to the invention.

As already mentioned, in a preferred embodiment of the invention the cosmetic, dermatological or pharmaceutical compositions according to the invention comprise no compounds selected from the group consisting of sorbitol and sorbitol esters. However, if the cosmetic, dermatological or pharmaceutical compositions according to the invention do comprise one or more compounds selected from the group consisting of sorbitol and sorbitol esters (where the carboxylic acid on which the acid component of these esters is based is preferably caprylic acid), these compounds together are preferably present in the cosmetic, dermatological or pharmaceutical compositions according to the invention in an amount smaller than or equal to 0.1% by weight, particularly preferably in an amount smaller than or equal to 0.06% by weight, most preferably in an amount smaller than or equal to 0.02% by weight and most preferably in an amount smaller than or equal to 0.01% by weight, the stated % by weight in each case being based on the total weight of the finished composition according to the invention.

As already mentioned, in a further preferred embodiment of the invention the cosmetic, dermatological or pharmaceutical compositions according to the invention comprise no compounds selected from the group consisting of sorbitan and sorbitan esters. However, if the cosmetic, dermatological or pharmaceutical compositions according to the invention do comprise one or more compounds selected from the group consisting of sorbitan and sorbitan esters (where the carboxylic acid on which the acid component of these esters is based is preferably caprylic acid), these compounds together are preferably present in the cosmetic, dermatological or pharmaceutical compositions according to the invention in an amount smaller than or equal to 0.4% by weight, particularly preferably in an amount smaller than or equal to 0.2% by weight, most preferably in an amount smaller than or equal to 0.1% by weight and most preferably in an amount smaller than or equal to 0.02% by weight, the stated % by weight in each case being based on the total weight of the finished composition according to the invention.

In a further preferred embodiment of the invention, the cosmetic, dermatological or pharmaceutical compositions according to the invention have viscosities preferably in the range from 50 to 200 000 mPa·s, particularly preferably in the range from 500 to 100 000 mPa·s, especially preferably in the range from 2000 to 50 000 mPa·s and most preferably in the range from 5000 to 30 000 mPa·s (20° C., Brookfield RVT, RV spindle set at 20 revolutions per minute).

In a further preferred embodiment of the invention, the cosmetic, dermatological or pharmaceutical compositions according to the invention are present in the form of fluids, gels, foams, sprays, lotions or creams.

The cosmetic, dermatological or pharmaceutical compositions according to the invention are preferably formulated on an aqueous or aqueous-alcoholic basis or are present as emulsions. Particularly preferably, they are present as emulsions, and especially preferably they are present as oil-in-water emulsions.

In a particularly preferred embodiment of the invention, the cosmetic, dermatological or pharmaceutical compositions according to the invention are present as oil-in-water emulsions and preferably comprise, based on the total weight of the compositions,
a) up to 95.0% by weight, preferably 49.49 to 95.0% by weight, particularly preferably 68.9 to 90.0% by weight, especially preferably 70.0 to 85.0% by weight, of an aqueous phase or an aqueous-alcoholic phase, b) up to 70.0% by weight, preferably 4.49 to 50.0% by weight, particularly preferably 8.9 to 30.0% by weight, especially preferably 13.5 to 25.0% by weight, of an oil phase,
c) up to 10.0% by weight, preferably 0.01 to 10.0% by weight, particularly preferably 0.1 to 5.0% by weight, especially preferably 0.5 to 2.0% by weight of a composition comprising one or more compounds of the formula (I) and one or more substances selected from the group consisting of hydroxypyridones and their salts, where the composition comprises the compounds and substances mentioned in an amount of preferably 30% by weight or more, particularly preferably 40% by weight or more and especially preferably 50% by weight or more, where furthermore the weight ratio of compounds of the formula (I): substances selected from the group consisting of hydroxypyridones and their salts is preferably from 2:1 to 30:1 and particularly preferably from 4:1 to 15:1 and where the composition is furthermore preferably a premix according to the invention and
d) up to 20.0% by weight, preferably 0.5 to 10.0% by weight, particularly preferably 1.0 to 5.0% by weight, especially preferably 1.0 to 3.0% by weight, of one or more further additives.

Preferably, the one or more further additives in the oil-in-water of emulsions just mentioned is/are selected from the group consisting of emulsifiers, coemulsifiers, solubilizers, active ingredients, sun protection filters, pigments and antimicrobially active compounds.

All mono- or polyhydric alcohols are suitable for the cosmetic, dermatological or pharmaceutical compositions according to the invention on an aqueous-alcoholic or else alcoholic basis. Preference is given to using alcohols having 1 to 4 carbon atoms, such as ethanol, propanol, isopropanol, n-butanol, isobutanol, t-butanol or glycerol, and also alkylene glycols, in particular propylene glycol, butylene glycol or hexylene glycol, and mixtures of said alcohols. Further preferred alcohols are polyethylene glycols with a relative molecular mass below 2000. Particular preference is given to using ethanol or isopropanol.

The cosmetic, dermatological or pharmaceutical compositions according to the invention may comprise one or more oils.

Advantageously, the oils may be selected from the groups of the triglycerides, natural and synthetic fatty substances, preferably esters of fatty acids with alcohols having a low carbon number, for example with methanol, isopropanol, propylene glycol or glycerol, or esters of fatty alcohols with alkanoic acids having a low carbon number or with fatty acids or from the group of the alkyl benzoates, and also natural or synthetic hydrocarbon oils.

Suitable are triglycerides of straight-chain or branched saturated or unsaturated, optionally hydroxylated $C_8$-$C_{30}$-fatty acids, in particular vegetable oils such as sunflower oil, corn oil, soybean oil, rice oil, jojoba oil, babassu oil, pumpkin oil, grapeseed oil, sesame oil, walnut oil, apricot oil, orange oil, wheatgerm oil, peach kernel oil, macadamia oil, avocado oil, sweet almond oil, lady's smock oil, castor oil, olive oil, peanut oil, rapeseed oil and coconut oil, and also synthetic triglyceride oils, for example the commercial product Myritol® 318. Hydrogenated triglycerides are also suitable. Oils of animal origin, for example beef tallow, perhydrosqualene, lanolin, can also be used.

A further class of preferred oily substances comprises the benzoic acid esters of linear or branched $C_{8-22}$-alkanols, for example the commercial products Finsolv® SB (isostearyl benzoate), Finsolv® TN ($C_{12}$-$C_{15}$-alkyl benzoate) and Finsolv® EB (ethylhexyl benzoate).

A further class of preferred oily substances comprises the dialkyl ethers having in total 12 to 36 carbon atoms, in particular having 12 to 24 carbon atoms, such as, for example, di-n-octyl ether (Cetiol® OE), di-n-nonyl ether, di-n-decyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether, di-3-ethyldecyl ether, tert-butyl n-octyl ether, isopentyl n-octyl ether and 2-methylpentyl n-octyl ether, and also di-tert-butyl ether and diisopentyl ether.

Branched saturated or unsaturated fatty alcohols having 6-30 carbon atoms, e.g. isostearyl alcohol, and Guerbet alcohols, are likewise suitable.

A further class of preferred oily substances comprises hydroxycarboxylic acid alkyl esters. Preferred hydroxycarboxylic acid alkyl esters are full esters of glycolic acid, lactic acid, malic acid, tartaric acid or citric acid. Further esters of hydroxycarboxylic acids which are suitable in principle are esters of β-hydroxypropionic acid, of tartronic acid, of D-gluconic acid, sugar acid, mucic acid or glucuronic acid. Suitable alcohol components of these esters are primary straight-chain or branched aliphatic alcohols having 8 to 22 carbon atoms. Here, the esters of $C_{12}$-$C_{15}$-fatty alcohols are particularly preferred. Esters of this type are commercially available, e.g. under the trade name Cosmacol® from EniChem, Augusta Industriale.

A further class of preferred oily substances comprises dicarboxylic acid esters of straight-chain or branched $C_2$-$C_{10}$-alkanols, such as di-n-butyl adipate (Cetiol® B), di(2-ethylhexyl)adipate and di(2-ethylhexyl) succinate, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate, and also diisotridecyl azelate.

Likewise preferred oily substances are symmetrical, asymmetrical or cyclic esters of carbonic acid with fatty alcohols, glycerol carbonate or dicaprylyl carbonate (Cetiol® CC).

A further class of preferred oily substances comprises the esters of dimers of unsaturated $C_{12}$-$C_{22}$-fatty acids (dimer fatty acids) with monohydric straight-chain, branched or cyclic $C_2$-$C_{18}$-alkanols or with polyhydric straight-chain or branched $C_2$-$C_6$-alkanols.

A further class of preferred oily substances comprises hydrocarbon oils, for example those with straight-chain or branched, saturated or unsaturated $C_7$-$C_{40}$-carbon chains, for example Vaseline, dodecane, isododecane, cholesterol, lanolin, synthetic hydrocarbons such as polyolefins, in particular polyisobutene, hydrogenated polyisobutene, polydecane, and hexadecane, isohexadecane, paraffin oils, isoparaffin oils, for example the commercial products of the Permethyl® series, squalane, squalene, and alicyclic hydrocarbons, for example the commercial product 1,3-di(2-ethylhexyl)cyclohexane (Cetiol® S), ozokerite, and ceresine.

Also suitable are silicone oils and silicone waxes, preferably dimethylpolysiloxanes and cyclomethicones, polydialkylsiloxanes $R_3SiO(R_2SiO)_xSiR_3$, where R is methyl or ethyl, particularly preferably methyl, and x is a number from 2 to 500, for example the dimethicones available under the trade names VICASIL (General Electric Company), DOW CORNING 200, DOW CORNING 225, DOW CORNING 200 (Dow Corning Corporation), and also the dimethicones available under SilCare® Silicone 41 M65, SilCare® Silicone 41 M70, SilCare® Silicone 41 M80 (Clariant), stearyldimethylpolysiloxane, $C_{20}$-$C_{24}$-alkyldimethylpolysiloxane, $C_{24}$-$C_{28}$-alkyldimethylpolysiloxane; but also the methicones available under SilCare® Silicone 41 M40, Sil- Care® Silicone 41 M50 (Clariant), furthermore trimethylsiloxysilicates $[(CH_2)_3SiO)_{1/2}]_x[SiO_2]_y$, where x is a number from 1 to 500 and y is a number from 1 to 500, dimethiconols $R_3SiO[R_2SiO]_xSiR_2OH$ and $HOR_2SiO[R_2SiO]_xSiR_2OH$, where R is methyl or ethyl and x is a number up to 500, polyalkylarylsiloxanes, for example the polymethylphenylsiloxanes available under the trade names SF 1075 METHYLPHENYL FLUID (General Electric Company) and 556 COSMETIC GRADE PHENYL TRIMETHICONE FLUID (Dow Corning Corporation), polydiarylsiloxanes, silicone resins, cyclic silicones and amino-, fatty-acid-, alcohol-, polyether-, epoxy-, fluorine- and/or alkyl-modified silicone compounds, and also polyether siloxane copolymers.

As further auxiliaries and additives, the cosmetic, dermatological or pharmaceutical compositions according to the invention may comprise, for example, waxes, emulsifiers, co-emulsifiers, solubilizers, electrolytes, hydroxy acids, stabilizers, cationic polymers, film formers, further thickeners, gelling agents, superfattening agents, refattening agents, further antimicrobially active compounds, biogenic active compounds, adstringents, deodorizing compounds sun protection filters, antioxidants, moisturizers, solvents, colorants, pearlizing agents, fragrances, opacifiers and/or silicones.

The cosmetic, dermatological or pharmaceutical compositions according to the invention may comprise waxes, for example paraffin waxes, microwaxes and ozokerites, beeswax and its partial fractions, and also beeswax derivatives, waxes from the group of homopolymeric polyethylenes or copolymers of α-olefins, and natural waxes such as rice wax, candelilla wax, carnauba wax, Japan wax or shellac wax.

Emulsifiers, coemulsifiers and solubilizers which can be used are nonionic, anionic, cationic or amphoteric surface-active compounds.

Suitable nonionic surface-active compounds are preferably:
addition products of from 1 to 30 mol of ethylene oxide and/or 1 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group and onto sorbitan or sorbitol esters; ($C_{12}$-$C_{18}$)-fatty acid mono- and diesters of addition products of from 1 to 30 mol of ethylene oxide onto glycerol; glycerol mono- and diesters and sorbitan mono- and diesters of saturated and unsaturated fatty acids having 14 to 22 carbon atoms and optionally ethylene oxide addition products thereof; addition products of from 15 to 60 mol of ethylene oxide onto castor oil and/or hydrogenated castor oil; polyol and in particular polyglycerol esters, such as, for example, polyglycerol polyricinoleate and polyglycerol poly-12-hydroxystearate. Ethoxylated fatty amines, fatty acid amides, fatty acid alkanolamides and mixtures of compounds of two or more of these substance classes are likewise preferably suitable.

Suitable ionogenic coemulsifiers are, for example, anionic emulsifiers, such as mono-, di- or triphosphoric acid esters, soaps (e.g. sodium stearate), fatty alcohol sulfates, but also cationic emulsifiers such as mono-, di- and trialkyl quats and polymeric derivatives thereof.

Available amphoteric emulsifiers are preferably alkylaminoalkylcarboxylic acids, betaines, sulfobetaines and imidazoline derivatives.

Particular preference is given to using fatty alcohol ethoxylates selected from the group of ethoxylated stearyl alcohols, isostearyl alcohols, cetyl alcohols, isocetyl alcohols, oleyl alcohols, lauryl alcohols, isolauryl alcohols and cetylstearyl alcohols, in particular polyethylene glycol(13) stearyl ether, polyethylene glycol(14) stearyl ether, polyethylene glycol(15) stearyl ether, polyethylene glycol(16) stearyl ether, polyethylene glycol(17) stearyl ether, polyethylene glycol(18) stearyl ether, polyethylene glycol(19) stearyl ether, polyethylene glycol(20) stearyl ether, polyethylene glycol(12) isostearyl ether, polyethylene glycol(13) isostearyl ether, polyethylene glycol(14) isostearyl ether, polyethylene glycol(15) isostearyl ether, polyethylene glycol(16) isostearyl ether, polyethylene glycol(17) isostearyl ether, polyethylene glycol(18) isostearyl ether, polyethylene glycol(19) isostearyl ether, polyethylene glycol(20) isostearyl ether, polyethylene glycol(13) cetyl ether, polyethylene glycol(14) cetyl ether, polyethylene glycol(15) cetyl ether, polyethylene glycol(16) cetyl ether, polyethylene glycol(17) cetyl ether, polyethylene glycol(18) cetyl ether, polyethylene glycol(19) cetyl ether, polyethylene glycol(20) cetyl ether, polyethylene glycol(13) isocetyl ether, polyethylene glycol(14) isocetyl ether, polyethylene glycol(15) isocetyl ether, polyethylene glycol(16) isocetyl ether, polyethylene glycol(17) isocetyl ether, polyethylene glycol(18) isocetyl ether, polyethylene glycol(19) isocetyl ether, polyethylene glycol(20) isocetyl ether, polyethylene glycol(12) oleyl ether, polyethylene glycol(13) oleyl ether, polyethylene glycol(14) oleyl ether, polyethylene glycol(15) oleyl ether, polyethylene glycol(12) lauryl ether, polyethylene glycol(12) isolauryl ether, polyethylene glycol(13) cetylstearyl ether, polyethylene glycol(14) cetylstearyl ether, polyethylene glycol(15) cetylstearyl ether, polyethylene glycol(16) cetylstearyl ether, polyethylene glycol(17) cetylstearyl ether, polyethylene glycol(18) cetylstearyl ether, polyethylene glycol(19) cetylstearyl ether.

Fatty acid ethoxylates selected from the group consisting of ethoxylated stearates, isostearates and oleates, in particular polyethylene glycol(20) stearate, polyethylene glycol(21) stearate, polyethylene glycol(22) stearate, polyethylene glycol(23) stearate, polyethylene glycol(24) stearate, polyethylene glycol(25) stearate, polyethylene glycol(12) isostearate, polyethylene glycol(13) isostearate, polyethylene glycol(14) isostearate, polyethylene glycol(15) isostearate, polyethylene glycol(16) isostearate, polyethylene glycol(17) isostearate, polyethylene glycol(18) isostearate, polyethylene glycol(19) isostearate, polyethylene glycol(20) isostearate, polyethylene glycol(21) isostearate, polyethylene glycol(22) isostearate, polyethylene glycol(23) isostearate, polyethylene glycol(24) isostearate, polyethylene glycol(25) isostearate, polyethylene glycol(12) oleate, polyethylene glycol(13) oleate, polyethylene glycol(14) oleate, polyethylene glycol(15) oleate, polyethylene glycol(16) oleate, polyethylene glycol(17) oleate, polyethylene glycol(18) oleate, polyethylene glycol(19) oleate, polyethylene glycol(20)oleate, are likewise preferred.

Sodium laureth-11 carboxylate can advantageously be used as ethoxylated alkylether carboxylic acid or salts thereof.

Ethoxylated triglycerides which can be used advantageously are polyethylene glycol(60) evening primrose glycerides.

It is furthermore advantageous to select the polyethylene glycol glycerol fatty acid esters from the group consisting of polyethylene glycol(20) glyceryl laurate, polyethylene glycol (6) glyceryl caprate/caprinate, polyethylene glycol(20) glyceryl oleate, polyethylene glycol(20) glyceryl isostearate and polyethylene glycol(18) glyceryl oleate/cocoate.

From among the ethoxylated sorbitan esters, polyethylene glycol(20) sorbitan monolaurate, polyethylene glycol(20) sorbitan monostearate, polyethylene glycol(20) sorbitan monoisostearate, polyethylene glycol(20) sorbitan monopalmitate, polyethylene glycol(20) sorbitan monooleate are particularly suitable.

Particularly advantageous coemulsifiers are glyceryl monostearate, glyceryl monooleate, diglyceryl monostearate, glyceryl isostearate, polyglyceryl-3 oleate, polyglyceryl-3 diisostearate, polyglyceryl-4 isostearate, polyglyceryl-2 dipolyhydroxystearate, polyglyceryl-4 dipolyhydroxystearate, PEG-30 dipolyhydroxystearate, diisostearoyl polyglyceryl-3 diisostearate, glycol distearate and polyglyceryl-3 dipolyhydroxystearate, sorbitan monoisostearate, sorbitan stearate, sorbitan oleate, sucrose distearate, lecithin, PEG-7-hydrogenated castor oil, cetyl alcohol, stearyl alcohol, behenyl alcohol, isobehenyl alcohol and polyethylene glycol(2) stearyl ether (steareth-2), alkylmethicone copolyols and alkyldimethicone copolyols, in particular cetyldimethicone copolyol (ABIL® EM 90), laurylmethicone copolyol or amodimethicone glycerocarbamate (Sil-Care® Silicone WSI, Clariant).

If the cosmetic, dermatological or pharmaceutical compositions according to the invention comprise one or more substances selected from the group consisting of emulsifiers, coemulsifiers and solubilizers, this one substance or these two or more substances is/are preferably present in the compositions according to the invention in an amount of from 0.1 to 20.0% by weight, particularly preferably in an amount of from 0.5 to 10.0% by weight and especially preferably in an amount of from 1.0 to 5.0% by weight, based on the total weight of the respective composition according to the invention.

Suitable for use as electrolyte are inorganic salts, preferably ammonium salts or metal salts, particularly preferably of halides, for example $CaCl_2$, $MgCl_2$, LiCl, KCl and NaCl, carbonates, bicarbonates, phosphates, sulfates, nitrates, especially preferably sodium chloride, and/or organic salts, preferably ammonium salts or metal salts, particularly preferably of glycolic acid, lactic acid, citric acid, tartaric acid, mandelic acid, salicylic acid, ascorbic acid, pyruvic acid, fumaric acid, retinoic acid, sulfonic acids, benzoic acid, kojic acid, fruit acid, malic acid, gluconic acid or galacturonic acid.

These also include aluminum salts, preferably aluminum chlorohydrate or aluminum-zirconium complex salts.

Accordingly, in a further preferred embodiment of the invention, the cosmetic, dermatological or pharmaceutical compositions according to the invention comprise one or more substances selected from the group consisting of inorganic and organic salts.

As electrolytes, the cosmetic, dermatological or pharmaceutical compositions according to the invention may also comprise mixtures of different salts.

If the cosmetic, dermatological or pharmaceutical compositions according to the invention comprise one or more electrolytes, these are preferably present in the compositions according to the invention in an amount of from 0.01 to 20.0% by weight, particularly preferably in an amount of from 0.1 to 10.0% by weight and especially preferably in an amount of from 0.5 to 5.0% by weight, based on the total weight of the respective composition according to the invention.

In a further preferred embodiment of the invention, the cosmetic, dermatological or pharmaceutical compositions according to the invention comprise one or more hydroxy acids, particularly preferably one or more substances selected from the group consisting of alpha- and beta-hydroxy acids.

As hydroxy acids, the cosmetic, dermatological or pharmaceutical compositions according to the invention may preferably comprise lactic acid, glycolic acid, salicylic acid and alkylated salicylic acids or citric acid. The cosmetic, dermatological or pharmaceutical compositions according to the invention may additionally comprise further acidic components. Suitable active compounds are tartaric acid, mandelic acid, caffeic acid, pyruvic acid, oligooxamono- and -dicarboxylic acids, fumaric acid, retinoic acid, sulfonic acids, benzoic acid, kojic acid, fruit acid, malic acid, gluconic acid, pyruvic acid, galacturonic acid, ribonic acid, and all their derivatives, polyglycoldioic acids in free or partially neutralized form, vitamin C (ascorbic acid), vitamin C derivatives, dihydroxyacetone or skin-whitening actives such as arbutin or glycyrrhetic acid and salts thereof. If the cosmetic, dermatological or pharmaceutical compositions according to the invention comprise one or more of these substances just mentioned, this one substance or these two or more substances is/are preferably present in the compositions according to the invention in an amount of from 0.1 to 20.0% by weight, particularly preferably in an amount of from 0.2 to 10.0% by weight and especially preferably in an amount of from 0.5 to 5.0% by weight, based on the total weight of the respective composition according to the invention.

In a further preferred embodiment of the invention, the cosmetic, dermatological or pharmaceutical compositions according to the invention therefore comprise one or more substances selected from the group consisting of vitamin C and vitamin C derivatives, where the vitamin C derivatives are preferably selected from the group consisting of sodium ascorbylphosphate, magnesium ascorbylphosphate and magnesium ascorbylglucoside.

In a further preferred embodiment of the invention, the cosmetic, dermatological or pharmaceutical compositions according to the invention therefore comprise one or more substances selected from the group consisting of benzoic acid, sorbic acid, salicylic acid, lactic acid and paramethoxybenzoic acid. The organic acids mentioned above may serve as further preservatives.

Stabilizers which can be used in the cosmetic, dermatological or pharmaceutical compositions according to the invention are metal salts of fatty acids, such as, for example, magnesium stearate, aluminum stearate and/or zinc stearate. If the cosmetic, dermatological or pharmaceutical compositions according to the invention comprise one or more of these substances just mentioned, this one substance or these two or more substances is/are preferably present in the compositions according to the invention in an amount of from 0.1 to 10.0% by weight, particularly preferably in an amount of from 0.5 to 8.0% by weight and especially preferably in an amount of from 1.0 to 5.0% by weight, based on the total weight of the respective composition according to the invention.

Suitable cationic polymers are those known under the INCI name "polyquaternium", in particular polyquaternium-31, polyquaternium-16, polyquaternium-24, polyquaternium-7, polyquaternium-22, polyquaternium-39, polyquaternium-28, polyquaternium-2, polyquaternium-10, polyquaternium-11, and polyquaternium 37& mineral oil & PPG trideceth (Salcare SC95), PVP-dimethylaminoethyl methacrylate copolymer, guar hydroxypropyltriammonium chlorides, and calcium alginate and ammonium alginate. Furthermore, use may be made of cationic cellulose derivatives; cationic starch; copolymers of diallylammonium salts and acrylamides; quaternized vinylpyrrolidone/vinylimidazole polymers; condensation products of polyglycols and amines; quaternized collagen polypeptides; quaternized wheat polypeptides; polyethyleneimines; cationic silicone polymers, such as, for example, amidomethicones; copolymers of adipic acid and dimethylaminohydroxypropyldiethylenetriamine; polyaminopolyamide and cationic chitin derivatives, such as, for example, chitosan.

If the cosmetic, dermatological or pharmaceutical compositions according to the invention comprise one or more of the cationic polymers mentioned above, these are preferably present in the compositions according to the invention in an amount of from 0.1 to 5.0% by weight, particularly preferably in an amount of from 0.2 to 3.0% by weight and especially preferably in an amount of from 0.5 to 2.0% by weight, based on the total weight of the respective composition according to the invention.

Furthermore, the cosmetic, dermatological or pharmaceutical compositions according to the invention may comprise film formers which, depending on the intended use, are selected from salts of phenylbenzimidazolesulfonic acid, water-soluble polyurethanes, for example $C_{10}$-polycarbamyl polyglyceryl ester, polyvinyl alcohol, polyvinylpyrrolidone copolymers, for example vinylpyrrolidone/vinyl acetate copolymer, or PVP/eicosene copolymers, maleinated polypropylene polymers, water-soluble acrylic acid polymers/copolymers and esters or salts thereof, for example partial ester copolymers of acrylic/methacrylic acid, water-soluble cellulose, for example hydroxymethylcellulose, hydroxyethylcellulose, hydroxypropylcellulose, water-soluble quaterniums, polyquaterniums, carboxyvinyl polymers, such as carbomers and salts thereof, polysaccharides, for example polydextrose and glucan, vinyl acetate/crotonate, for example available under the trade name Aristoflex® A 60 (Clariant).

If the cosmetic, dermatological or pharmaceutical compositions according to the invention comprise one or more filmformers, these are preferably present in the compositions according to the invention in an amount of from 0.1 to 10.0% by weight, particularly preferably in an amount of from 0.2 to 5.0% by weight and especially preferably in an amount of from 0.5 to 3.0% by weight, based on the total weight of the respective composition according to the invention.

The desired viscosity of the cosmetic, dermatological or pharmaceutical compositions can be established by adding further thickeners and gelling agents. Suitable are preferably cellulose ethers and other cellulose derivatives (e.g. carboxymethylcellulose, hydroxyethylcellulose), gelatin, starch and starch derivatives, sodium alginates, fatty acid polyethylene glycol esters, agar, carrageenan, tragacanth or dextrin derivatives, in particular dextrin esters. Furthermore suitable are metal salts of fatty acids, preferably having 12 to 22 carbon atoms, for example sodium stearate, sodium palmitate, sodium laurate, sodium arachidates, sodium behenate, potassium stearate, potassium palmitate, sodium myristate, aluminum monostearate, hydroxy fatty acids, for example 12-hydroxystearic acid, 16-hydroxyhexadecanoyl acid; fatty acid amides; fatty acid alkanolamides; dibenzalsorbitol and alcohol-soluble polyamides and polyacrylamides or mixtures of such. Use may furthermore be made of crosslinked and uncrosslinked polyacrylates such as carbomers, sodium polyacrylates or polymers containing sulfonic acid, such as ammonium acryloyldimethyltaurate/VP copolymer or sodium acryloyldimethyltaurate/VP copolymer.

If the cosmetic, dermatological or pharmaceutical compositions according to the invention comprise one or more substances selected from the group consisting of the further thickeners and gelling agents, this one substance or these two or more substances is/are preferably present in the compositions according to the invention in an amount of from 0.01 to 20.0% by weight, particularly preferably in an amount of from 0.1 to 10.0% by weight, especially preferably in an amount of from 0.2 to 3.0% by weight and most preferably in an amount of from 0.4 to 2.0% by weight, based on the total weight of the respective composition according to the invention.

Preferred for use as superfattening agents or refattening agents are lanolin and lecithin, non-ethoxylated and poly-ethoxylated or acylated lanolin and lecithin derivatives, polyol fatty acid esters such as glyceryl oleate, mono-, di- and triglycerides and/or fatty acid alkanolamides, the latter simultaneously serving as foam stabilizers. If the cosmetic, dermatological or pharmaceutical compositions according to the invention comprise one or more of the substances just mentioned, this one substance or these two or more substances is/are preferably present in the compositions according to the invention in an amount of from 0.01 to 10.0% by weight, particularly preferably in an amount of from 0.1 to 5.0% by weight and especially preferably in an amount of from 0.5 to 3.0% by weight, based on the total weight of the respective composition according to the invention.

In a further preferred embodiment of the invention, the cosmetic, dermatological or pharmaceutical compositions according to the invention comprise one or more further antimicrobially active compounds and are preferably present in the form of disinfectant compositions and particularly preferably in the form of disinfectant gels.

Further antimicrobially active compounds employed may be cetyltrimethyl-ammonium chloride, cetylpyridinium chloride, benzethonium chloride, diisobutylethoxyethyldimethylbenzylammonium chloride, sodium N-lauryl-sarcosinate, sodium N-palmethylsarcosinate, lauroylsarcosine, N-myristoylglycine, potassium N-laurylsarcosine, trimethylammonium chloride, sodium aluminum chlorohydroxylactate, triethyl citrate, tricetylmethylammonium chloride, 2,4,4'-trichloro-2'-hydroxydiphenyl ether (triclosan), phenoxyethanol, 1,5-pentanediol, 1,6-hexanediol, 3,4,4'-trichlorocarbanilide (triclocarban), diaminoalkylamide, for example L-lysine hexadecylamide, citrate heavy metal salts, salicylates, piroctoses, in particular zinc salts, pyrithiones and heavy metal salts thereof, in particular zinc pyrithione, zinc phenol sulfate, farnesol, ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, selenium disulfide, iodopropynyl butylcarbamate, methylchloroisothiazolinone, methylisothiazolinone, methyldibromoglutaronitrile, AgCl, chloroxylenol, Na salt of diethylhexyl sulfosuccinate, sodium benzoate, and phenoxyethanol, benzyl alcohol, phenoxyisopropanol, parabens, preferably butyl, ethyl, methyl and propyl paraben, and Na salts thereof, pentanediol, 1,2-octanediol, 2-bromo-2-nitropropane-1,3-diol, ethylhexylglycerol, benzyl alcohol, sorbic acid, benzoic acid, lactic acid, imidazolidinylurea, diazolidinylurea, dimethyloldimethylhydantoin (DMDMH), Na salt of hydroxymethylglycinate, hydroxyethylglycine of sorbic acid and combinations of these active substances.

If the cosmetic, dermatological or pharmaceutical compositions according to the invention comprise one or more further antimicrobially active compounds, these are preferably present in the compositions according to the invention in an amount of from 0.001 to 5.0% by weight, particularly preferably in an amount of from 0.01 to 3.0% by weight and especially preferably in an amount of from 0.1 to 2.0% by weight, based on the total weight of the respective composition according to the invention.

The cosmetic, dermatological or pharmaceutical compositions according to the invention may furthermore comprise biogenic active compounds selected from plant extracts, such as, for example, aloe vera, and also local anesthetics, antibiotics, antiphlogistics, antiallergics, corticosteroids, sebostatics, Bisabolol®, allantoin, Phytantriol®, proteins, vitamins selected from niacin, biotin, vitamin B2, vitamin B3, vitamin B6, vitamin B3 derivatives (salts, acids, esters, amides, alcohols), vitamin C and vitamin C derivatives (salts, acids, esters, amides, alcohols), preferably as sodium salt of the monophosphoric acid ester of ascorbic acid or as magnesium salt of the phosphoric acid ester of ascorbic acid, tocopherol and tocopherol acetate, and also vitamin E and/or derivatives thereof.

If the cosmetic, dermatological or pharmaceutical compositions according to the invention comprise one or more biogenic active compounds, these are preferably present in the compositions according to the invention in an amount of from 0.001 to 5.0% by weight, particularly preferably in an amount of from 0.01 to 3.0% by weight and especially preferably in an amount of from 0.1 to 2.0% by weight, based on the total weight of the respective composition according to the invention.

The cosmetic, dermatological or pharmaceutical compositions according to the invention may comprise astringents, preferably magnesium oxide, aluminum oxide, titanium dioxide, zirconium dioxide and zinc oxide, oxide hydrates, preferably aluminum oxide hydrate (boehmite) and hydroxides, preferably of calcium, magnesium, aluminum, titanium, zirconium or zinc, and also aluminum chlorohydrates. If the cosmetic, dermatological or pharmaceutical compositions according to the invention comprise one or more astringents, these are preferably present in the compositions according to the invention in an amount of from 0.001 to 50.0% by weight, particularly preferably in an amount of from 0.01 to 10.0% by weight and especially preferably in an amount of from 0.1 to 10.0% by weight, based on the total weight of the respective composition according to the invention.

Preferred deodorizing substances are allantoin and bisabolol. If the cosmetic, dermatological or pharmaceutical compositions according to the invention comprise one or more deodorizing substances, these are preferably present in the compositions according to the invention in an amount of from 0.0001 to 10.0% by weight, based on the total weight of the respective composition according to the invention.

In a further preferred embodiment of the invention, the cosmetic, dermatological or pharmaceutical compositions according to the invention comprise one or more substances selected from inorganic and organic UV filters and are particularly preferably present in the form of sun protection compositions.

As pigments/micropigments and as inorganic sun protection filters or UV filters, the cosmetic, dermatological or pharmaceutical compositions according to the invention may comprise microfine titanium dioxide, mica/titanium oxide, iron oxides, mica/iron oxide, zinc oxide, silicon oxides, ultramarine blue or chromium oxides.

The organic sun protection filters or UV filters are preferably selected from the group consisting of 4-aminobenzoic acid, 3-(4'-trimethylammonium)benzylidene-boran-2-one methyl sulfate, camphorbenzalkonium methosulfate, 3,3,5-trimethyl-cyclohexyl salicylate, 2-hydroxy-4-methoxybenzophenone, 2-phenylbenzimidazole-5-sulfonic acid and its potassium, sodium and triethanolamine salts, 3,3'-(1,4-phenylenedimethine)bis(7,7-dimethyl-2-oxobicyclo[2.2.1]heptane-1-methanesulfonic acid) and its salts, 1-(4-tert-butylphenyl)-3-(4-methoxyphenyl)-propane-1,3-dione, 3-(4'-sulfo)benzylidenebornan-2-one and its salts, 2-ethylhexyl 2-cyano-3,3-diphenylacrylate, polymers of N-[2(and 4)-(2-oxoborn-3-ylidene-methyl)benzyl]acrylamide, 2-ethylhexyl 4-methoxycinnamate, ethoxylated ethyl 4-aminobenzoate, isoamyl 4-methoxycinnamate, 2,4,6-tris[p-(2-ethylhexyloxy-carbonyl)anilino]-1,3,5-triazine, 2-(2H-benzotriazol-2-yl)-4-methyl-6-(2-methyl-3-(1,3,3,3-tetramethyl-1-(trimethylsilyloxy)disiloxanyl)propyl)phenol, bis(2-ethylhexyl) 4,4'-[(6-[4-((1,1-dimethylethyl)aminocarbonyl)phenylamino]-1,3,5-triazin-2,4-yl)diimino]bisbenzoate, benzophenone-3, benzophenone-4 (acid), 3-(4'-methyl-benzylidene)-D,L-camphor, 3-benzylidenecamphor, 2-ethylhexyl salicylate, 2-ethylhexyl 4-dimethylaminobenzoate, hydroxy-4-methoxybenzophenone-5-sulfonic acid (sulfisobenzone) and the sodium salt, 4-isopropylbenzyl salicylate, N,N,N-trimethyl-4-(2-oxoborn-3-ylidenemethyl)anilium methyl sulfate, homosalate (INN), oxybenzone (INN), 2-phenylbenzimidazole-5-sulfonic acid and its sodium, potassium and triethanolamine salts, octylmethoxycinnamic acid, isopentyl-4-methoxycinnamic acid, isoamyl-p-methoxycinnamic acid, 2,4,6-trianilino(p-carbo-2'-ethylhexyl-1'-oxy)-1,3,5-triazine (octyltriazone) phenol, 2-2(2H-benzotriazol-2-yl)-4-methyl-6-(2-methyl-3-(1,3,3,3-tetramethyl-1-(trimethylsilyl)oxy)disiloxanyl) propyl(drometrizoletrisiloxane)benzoic acid, 4,4'-((6-(((1,1-dimethylethyl)amino)-carbonyl)phenyl)amino)-1,3,5-triazine-2,4-diyl)diimino)bis,bis(2-ethylhexyl) ester)benzoic acid, 4,4'-((6-(((1,1-dimethylethyl)amino)carbonyl)phenyl)amino)-1,3,5-triazine-2,4-diyl)diimino)bis,bis(2-ethylhexyl)ester), 3-(4'-methylbenzylidene)-D,L-camphor (4-methylbenzylidenecamphor), benzylidenecamphorsulfonic acid, octocrylene, polyacrylamidomethylbenzylidenecamphor, 2-ethylhexyl salicylate (octylsalicylate), ethyl-2-hexyl 4-dimethylaminobenzoate (octyldimethyl PABA), PEG-25 PABA, 2-hydroxy-4-methoxybenzophenone-5-sulfonic acid (benzophenone-5) and the Na salt, 2,2'-methylenebis-6-(2H-benzotriazol-2-yl)-4-(tetramethylbutyl)-1,1,3,3-phenol, sodium salt of 2-2'-bis(1,4-phenylene)-1H-benzimidazole-4,6-disulfonic acid, (1,3,5)-triazine-2,4-bis((4-(2-ethylhexyloxy)-2-hydroxy)phenyl)-6-(4-methoxyphenyl), 2-ethylhexyl 2-cyano-3,3-diphenyl-2-propenoate, glyceryl octanoate, di-p-methoxycinnamic acid, p-aminobenzoic acid and esters thereof, 4-tert-butyl-4'-methoxydibenzoylmethane, 4-(2-β-glucopyranoxy)propoxy-2-hydroxybenzophenone, octyl salicylate, methyl-2,5-diisopropylcinnamic acid, cinoxate, dihydroxydimethoxybenzophenone, disodium salt of 2,2'-dihydroxy-4,4'-dimethoxy-5,5'-disulfobenzophenone, dihydroxy-benzophenone, 1,3,4-dimethoxyphenyl-4,4-dimethyl-1,3-pentanedione, 2-ethylhexyl dimethoxybenzylidenedioxoimidazolidinepropionate, methylenebisbenzo-triazolyl tetramethylbutylphenol, phenyl dibenzimidazoletetrasulfonate, bis-ethylhexyloxyphenol methoxyphenol triazine, tetrahydroxybenzophenones, terephthalylidenedicamphorsulfonic acid, 2,4,6-tris[4,2-ethylhexyloxycarbonyl)-anilino}-1,3,5-triazine, methylbis(trimethylsiloxy)silylisopentyltrimethoxycinnamic acid, amyl p-dimethylaminobenzoate, amyl p-dimethylaminobenzoate, 2-ethylhexyl p-dimethylaminobenzoate, isopropyl-p-methoxycinnamic acid/diisopropylcinnamic acid esters, 2-ethylhexyl-p-methoxycinnamic acid, 2-hydroxy-4-methoxybenzophenone, 2-hydroxy-4-methoxybenzophenone-5-sulfonic acid and the trihydrate, and also 2-hydroxy-4-methoxybenzophenone-5-sulfonate sodium salt and phenylbenzimidazolesulfonic acid.

If the cosmetic, dermatological or pharmaceutical compositions according to the invention comprise one or more sun protection filters, these are preferably present in the compositions according to the invention in an amount of from 0.001 to 30.0% by weight, particularly preferably in an amount of from 0.05 to 20.0% by weight and especially preferably in an amount of from 1.0 to 10.0% by weight, based on the total weight of the respective composition according to the invention.

The cosmetic, dermatological or pharmaceutical compositions according to the invention may comprise one or more antioxidants, preferably selected from the group consisting of amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g, thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof), and also salts thereof, dilauryl thiodipropionate, distearyl thiodipropionate, thiodipropionic acid and derivatives thereof (e.g. esters, ethers, peptides, lipids, nucleotides, nucleosides and salts), and also sulfoximine compounds (e.g. buthionine sulfoximines, homocysteine sulfoximine, buthionine sulfones, penta-, hexa-, heptathionine sulfoximine) in very low tolerated doses, also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide), superoxide dismutase and the derivatives suitable according to the invention (salts, esters, ethers, sugars, nucleotides, nucleosides, peptides and lipids) of these specified substances.

The antioxidants can protect the skin and the hair against oxidative stress. Preferred antioxidants here are vitamin E and derivatives thereof, and vitamin A and derivatives thereof.

If the cosmetic, dermatological or pharmaceutical compositions according to the invention comprise one or more antioxidants, these are preferably present in the compositions according to the invention in an amount of from 0.001 to 30.0% by weight, particularly preferably in an amount of from 0.05 to 20.0% by weight and especially preferably in an amount of from 1.0 to 10.0% by weight, based on the total weight of the respective composition according to the invention.

Furthermore, humectants selected from the group consisting of the sodium salt of 2-pyrrolidone-5-carboxylate (NaPCA), guanidine; glycolic acid and salts thereof, lactic acid and salts thereof, glucosamines and salts thereof, lactamide monoethanolamine, acetamide monoethanolamine, urea, hydroxyethylurea, hydroxy acids, panthenol and derivatives thereof, for example D-panthenol (R-2,4-dihydroxy-N-(3-hydroxypropyl)-3,3-dimethylbutamide), D,L-panthenol, calcium pantothenate, panthetine, pantotheine, panthenyl ethyl ether, isopropyl palmitate and/or glycerol may be employed. If the compositions according to the invention comprise one or more humectants, these are preferably present in the compositions according to the invention in an amount of from 0.1 to 15.0% by weight and particularly preferably in an amount of from 0.5 to 5.0% by weight, based on the total weight of the respective composition according to the invention.

The cosmetic, dermatological or pharmaceutical compositions according to the invention may additionally comprise organic solvents. In principle, suitable organic solvents are all mono- or polyhydric alcohols. Preference is given to using alcohols having 1 to 4 carbon atoms, such as ethanol, propanol, isopropanol, n-butanol, isobutanol, t-butanol, glycerol and mixtures of said alcohols. Further preferred alcohols are polyethylene glycols with a relative molecular mass below 2000. In particular, a use of polyethylene glycol with a relative molecular mass between 200 and 600 and in amounts up to 45.0% by weight and of polyethylene glycol with a relative molecular mass between 400 and 600 in amounts of from 5.0 to 25.0% by weight is preferred. Further suitable solvents are, for example, triacetin (glycerol triacetate) and 1-methoxy-2-propanol.

The cosmetic, dermatological or pharmaceutical compositions according to the invention may comprise one or more substances selected from colorants, e.g. dyes and/or pigments. The dyes and/or pigments present in the cosmetic, dermatological or pharmaceutical compositions according to the invention, both organic and inorganic dyes and pigments, are selected from the corresponding positive list of the Cosmetics Regulations or the EC list of cosmetic colorants.

| Chemical or other name | CIN | Color |
| --- | --- | --- |
| Pigment Green | 10006 | green |
| Acid Green 1 | 10020 | green |
| 2,4-dinitrohydroxynaphthalene-7-sulfonic acid | 10316 | yellow |
| Pigment Yellow 1 | 11680 | yellow |
| Pigment Yellow 3 | 11710 | yellow |
| Pigment Orange 1 | 11725 | orange |
| 2,4-dihydroxyazobenzene | 11920 | orange |
| Solvent Red 3 | 12010 | red |
| 1-(2'-chloro-4'-nitro-1'-phenylazo)-2-hydroxynaphthalene | 12085 | red |
| Pigment Red 3 | 12120 | red |
| Ceres Red; Sudan Red; Fat Red G | 12150 | red |
| Pigment Red 112 | 12370 | red |
| Pigment Red 7 | 12420 | red |
| Pigment Brown 1 | 12480 | brown |
| 4-(2'-methoxy-5'-sulfonic acid diethylamide-1'-phenylazo)-3-hydroxy-5''-chloro-2'',4''-dimethoxy-2-naphthoic anilide | 12490 | red |
| Disperse Yellow 16 | 12700 | yellow |
| 1-(4-sulfo-1-phenylazo)-4-aminobenzenesulfonic acid | 13015 | yellow |
| 2,4-dihydroxyazobenzene-4'-sulfonic acid | 14270 | orange |
| 2-(2,4-dimethylphenylazo-5-sulfonic acid)-1-hydroxynaphthalene-4-sulfonic acid | 14700 | red |
| 2-(4-sulfo-1-naphthylazo)-1-naphthol-4-sulfonic acid | 14720 | red |
| 2-(6-sulfo-2,4-xylylazo)-1-naphthol-5-sulfonic acid | 14815 | red |
| 1-(4'-sulfophenylazo)-2-hydroxynaphthalene | 15510 | orange |
| 1-(2-sulfonic acid-4-chloro-5-carboxylic acid-1-phenylazo)-2-hydroxynaphthalene | 15525 | red |
| 1-(3-methylphenylazo-4-sulfonic acid)-2-hydroxynaphthalene | 15580 | red |
| 1-(4',(8')-sulfonic acid naphthylazo)-2-hydroxynaphthalene | 15620 | red |
| 2-hydroxy-1,2'-azonaphthalene-1'-sulfonic acid | 15630 | red |
| 3-hydroxy-4-phenylazo-2-naphthylcarboxylic acid | 15800 | red |
| 1-(2-sulfo-4-methyl-1-phenylazo)-2-naphthylcarboxylic acid | 15850 | red |
| 1-(2-sulfo-4-methyl-5-chloro-1-phenylazo)-2-hydroxynaphthalene-3-carboxylic acid | 15865 | red |
| 1-(2-sulfo-1-naphthylazo)-2-hydroxynaphthalene-3-carboxylic acid | 15880 | red |
| 1-(3-sulfo-1-phenylazo)-2-naphthol-6-sulfonic acid | 15980 | orange |

| Chemical or other name | CIN | Color |
| --- | --- | --- |
| 1-(4-sulfo-1-phenylazo)-2-naphthol-6-sulfonic acid | 15985 | yellow |
| Allura Red | 16035 | red |
| 1-(4-sulfo-1-naphthylazo)-2-naphthol-3,6-disulfonic acid | 16185 | red |
| Acid Orange 10 | 16230 | orange |
| 1-(4-sulfo-1-naphthylazo)-2-naphthol-6,8-disulfonic acid | 16255 | red |
| 1-(4-sulfo-1-naphthylazo)-2-naphthol-3,6,8-trisulfonic acid | 16290 | red |
| 8-amino-2-phenylazo-1-naphthol-3,6-disulfonic acid | 17200 | red |
| Acid Red 1 | 18050 | red |
| Acid Red 155 | 18130 | red |
| Acid Yellow 121 | 18690 | yellow |
| Acid Red 180 | 18736 | red |
| Acid Yellow 11 | 18820 | yellow |
| Acid Yellow 17 | 18965 | yellow |
| 4-(4-sulfo-1-phenylazo)-1-(4-sulfophenyl)-5-hydroxyphrazolone-3-carboxylic acid | 19140 | yellow |
| Pigment Yellow 16 | 20040 | yellow |
| 2,6-(4'-sulfo-2'',4''-dimethyl)-bis-phenylazo)1,3-dihydroxybenzene | 20170 | orange |
| Acid Black 1 | 20470 | black |
| Pigment Yellow 13 | 21100 | yellow |
| Pigment Yellow 83 | 21108 | yellow |
| Solvent Yellow | 21230 | yellow |
| Acid Red 163 | 24790 | red |
| Acid Red 73 | 27290 | red |
| 2-[4'-(4''-sulfo-1''-phenylazo)-7'-sulfo-1'-naphthylazo]-1-hydroxy-7-aminonaphthalene-3,6-disulfonic acid | 27755 | black |
| 4'-[(4''-sulfo-1''-phenylazo)-7'-sulfo-1'-naphthylazo]-1-hydroxy-8-acetylaminonaphthalene-3,5-disulfonic acid | 28440 | black |
| Direct Orange 34, 39, 44, 46, 60 | 40215 | orange |
| Food Yellow | 40800 | orange |
| trans-β-apo-8'-carotinaldehyde ($C_{30}$) | 40820 | orange |
| trans-apo-8'-carotic acid ($C_{30}$)-ethyl ester | 40825 | orange |
| canthaxanthin | 40850 | orange |
| Acid Blue 1 | 42045 | blue |
| 2,4-disulfo-5-hydroxy-4'-4''-bis(diethylamino)triphenylcarbinol | 42051 | blue |
| 4-[(4-N-ethyl-p-sulfobenzylamino)phenyl(4-hydroxy-2-sulfophenyl)(methylene)-1-(N-ethyl-N-p-sulfobenzyl)-2,5-cyclohexadienimine] | 42053 | green |
| Acid Blue 7 | 42080 | blue |
| (N-ethyl-p-sulfobenzylaminophenyl-(2-sulfophenyl)methylene-(N-ethyl-N-p-sulfobenzyl)cyclohexadienimine | 42090 | blue |
| Acid Green 9 | 42100 | green |
| diethyldisulfobenzyl-di-4-amino-2-chlorodi-2-methylfuchsonimmonium | 42170 | green |
| Basic Violet 14 | 42510 | violet |
| Basic Violet 2 | 42520 | violet |
| 2'-methyl-4'-(N-ethyl-N-m-sulfobenzyl)amino-4''-(N-diethyl)amino-2-methyl-N-ethyl-N-m-sulfobenzylfuchsonimmonium | 42735 | blue |
| 4'-(N-dimethyl)amino-4''-(N-phenyl)aminonaphtho-N-dimethylfuchsonimmonium | 44045 | blue |
| 2-hydroxy-3,6-disulfo-4,4'-bisdimethylaminonaphthofuchsinimmonium | 44090 | green |
| Acid Red | 45100 | red |
| 3-(2'-methylphenylamino)-6-(2'-methyl-4'-sulfophenylamino)-9-(2''-carboxyphenyl)xanthenium salt | 45190 | violet |
| Acid Red 50 | 45220 | red |
| phenyl-2-oxyfluorone-2-carboxylic acid | 45350 | yellow |
| 4,5-dibromofluorescein | 45370 | orange |
| 2,4,5,7-tetrabromofluorescein | 45380 | red |
| Solvent Dye | 45396 | orange |
| Acid Red 98 | 45405 | red |
| 3'4'5'6'-tetrachloro-2,4,5,7-tetrabromofluorescein | 45410 | red |
| 4,5-diiodofluorescein | 45425 | red |
| 2,4,5,7-tetraiodofluorescein | 45430 | red |
| quinophthalone | 47000 | yellow |
| quinophthalonedisulfonic acid | 47005 | yellow |
| Acid Violet 50 | 50325 | violet |
| Acid Black 2 | 50420 | black |
| Pigment Violet 23 | 51319 | violet |
| 1,2-dioxyanthraquinone, calcium-aluminum complex | 58000 | red |
| 3-oxypyrene-5,8,10-sulfonic acid | 59040 | green |
| 1-hydroxy-4-N-phenylaminoanthraquinone | 60724 | violet |
| 1-hydroxy-4-(4'-methylphenylamino)anthraquinone | 60725 | violet |
| Acid Violet 23 | 60730 | violet |
| 1,4-di(4'-methylphenylamino)anthraquinone | 61565 | green |
| 1,4-bis(o-sulfo-p-toluidine)anthraquinone | 61570 | green |
| Acid Blue 80 | 61585 | blue |
| Acid Blue 62 | 62045 | blue |
| N,N'-dihydro-1,2,1',2'-anthraquinonazine | 69800 | blue |
| Vat Blue 6; Pigment Blue 64 | 69825 | blue |
| Vat Orange 7 | 71105 | orange |
| indigo | 73000 | blue |
| indigodisulfonic acid | 73015 | blue |
| 4,4'-dimethyl-6,6'-dichlorothioindigo | 73360 | red |
| 5,5'-dichloro-7,7'-dimethylthioindigo | 73385 | violet |
| Quinacridone Violet 19 | 73900 | violet |
| Pigment Red 122 | 73915 | red |
| Pigment Blue 16 | 74100 | blue |
| phthalocyanine | 74160 | blue |
| Direct Blue 86 | 74180 | blue |
| chlorinated phthalocyanines | 74260 | green |
| Natural Yellow 6, 19; Natural Red 1 | 75100 | yellow |
| bixin, norbixin | 75120 | orange |
| lycopene | 75125 | yellow |
| trans-alpha, beta- or gamma-carotene | 75130 | orange |
| keto- and/or hydroxyl derivatives of carotene | 75135 | yellow |
| guanine or pearlescent agents | 75170 | white |
| 1,7-bis(4-hydroxy-3-methoxyphenyl)-1,6-heptadiene-3,5-dione | 75300 | yellow |
| complex salt (Na, Al, Ca) of carminic acid | 75470 | red |
| chlorophyll a and b; copper compounds of chlorophylls and chlorophyllins | 75810 | green |
| aluminum | 77000 | white |
| alumina hydrate | 77002 | white |
| water-containing aluminum silicates | 77004 | white |
| ultramarine | 77007 | blue |
| Pigment Red 101 and 102 | 77015 | red |
| barium sulfate | 77120 | white |
| bismuth oxychloride and mixtures thereof with mica | 77163 | white |
| calcium carbonate | 77220 | white |
| calcium sulfate | 77231 | white |
| carbon | 77266 | black |
| Pigment Black 9 | 77267 | black |
| Carbo medicinalis vegetabilis | 77268:1 | black |
| chromium oxide | 77288 | green |
| chromium oxide, water-containing | 77289 | green |
| Pigment Blue 28, Pigment Green 14 | 77346 | green |
| Pigment Metal 2 | 77400 | brown |
| gold | 77480 | brown |
| iron oxides and hydroxides | 77489 | orange |
| iron oxides and hydroxides | 77491 | red |
| iron oxide hydrate | 77492 | yellow |
| iron oxide | 77499 | black |
| mixtures of iron(II) and iron(III) hexacyanoferrate | 77510 | blue |
| Pigment White 18 | 77713 | white |
| manganese ammonium diphosphate | 77742 | violet |
| manganese phosphate; $Mn_3(PO_4)_2 \cdot 7H_2O$ | 77745 | red |
| silver | 77820 | white |
| titanium dioxide and mixtures thereof with mica | 77891 | white |
| zinc oxide | 77947 | white |
| 6,7-dimethyl-9-(1'-D-ribityl)isoalloxazine, lactoflavin | | yellow |
| caramel | | brown |
| capsanthin, capsorubin | | orange |
| betanin | | red |
| benzopyrilium salts, anthocyanines | | red |
| aluminum stearate, zinc stearate, magnesium stearate and calcium stearate | | white |
| Bromothymol Blue | | blue |
| Bromocresol Green | | green |
| Acid Red 195 | | red |

Oil-soluble natural dyes, such as, for example, paprika extracts, β-carotene and cochineal are furthermore advantageous.

Also advantageously used are pearlescent pigments, e.g. pearl essence (guanine/hypoxanthine mixed crystals from fish scales) and mother of pearl (ground seashells), monocrystalline pearlescent pigments such as, for example, bismuth oxychloride (BiOCl), layer substrate pigments, e.g. mica/metal oxide, silver-white pearlescent pigments from $TiO_2$, interference pigments ($TiO_2$, variable layer thickness), color luster pigments ($Fe_2O_3$) and combination pigments ($TiO_2$/$Fe_2O_3$, $TiO_2$/$Cr_2O_3$, $TiO_2$/Prussian blue, $TiO_2$/carmine).

Effect pigments within the context of the present invention are understood as meaning pigments which by virtue of their refraction properties produce special optical effects. Effect pigments impart to the treated surface (skin, hair, mucous membrane) luster or glitter effects or can visually conceal unevenness of the skin and skin wrinkles by means of diffuse light scattering. As a particular embodiment of the effect pigments, interference pigments are preferred. Particularly suitable effect pigments are, for example, mica particles which are coated with at least one metal oxide. Besides mica, a sheet silicate, silica gel and other $SiO_2$ modifications are also suitable as carriers. A metal oxide frequently used for coating is, for example, titanium oxide, to which, if desired, iron oxide can be admixed. By means of the size and shape (e.g. spherical, ellipsoidal, flat, even, uneven) of the pigment particles and by means of the thickness of the oxide coating, the reflection properties can be influenced. Also other metal oxides, e.g. bismuth oxychloride (BiOCl) and the oxides of, for example, titanium, in particular the $TiO_2$ modifications anatase and rutile, aluminum, tantalum, niobium, zirconium and hafnium. Effect pigments can also be prepared using magnesium fluoride ($MgF_2$) and calcium fluoride (fluorspar, $CaF_2$).

The effects can be controlled both by means of the particle size and by means of the particle size distribution of the pigment ensemble. Suitable particle size distributions extend, for example, from 2-50 µm, 5-25 µm, 5-40 µm, 5-60 µm, 5-95 µm, 5-100 µm, 10-60 µm, 10-100 µm, 10-125 µm, 20-100 µm, 20-150 µm, and <15 µm. A wider particle size distribution, for example of 20-150 µm, produces glittering effects, whereas a narrower particle size distribution of <15 µm provides for a uniform silky appearance.

If the cosmetic, dermatological or pharmaceutical compositions according to the invention comprise one or more effect pigments, these are preferably present in the compositions according to the invention in an amount of from 0.1 to 20.0% by weight, particularly preferably in an amount of from 0.5 to 10.0% by weight and especially preferably in an amount of from 1.0 to 5.0% by weight, based on the total weight of the respective composition according to the invention.

Preferably suitable as pearlizing component are fatty acid monoalkanolamides, fatty acid dialkanolamides, monoesters or diesters of alkylene glycols, in particular ethylene glycol and/or propylene glycol or oligomers thereof, with higher fatty acids, such as, for example, palmitic acid, stearic acid and behenic acid, monoesters or polyesters of glycerol with carboxylic acids, fatty acids and metal salts thereof, ketosulfones or mixtures of the specified compounds.

Particular preference is given to ethylene glycol distearates and/or polyethylene glycol distearates having on average 3 glycol units.

If the cosmetic, dermatological or pharmaceutical compositions according to the invention comprise one or more pearlizing compounds, these are preferably present in the compositions according to the invention in an amount of from 0.1 to 15.0% by weight and particularly preferably in an amount of from 1.0 to 10.0% by weight, based on the total weight of the respective composition according to the invention.

Fragrance and/or perfume oils which may be used are individual odorant compounds, e.g. the synthetic products of the ester, ether, aldehyde, ketone, alcohol and hydrocarbon types. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexyl propionate, styrallyl propionate and benzyl salicylate. The ethers include, for example, benzyl ethyl ethers, the aldehydes include, for example, the linear alkanals having 8 to 18 carbon atoms, citral, citronellal, citronellyloxyacetaldehyde, cyclamenaldehyde, hydroxycitronellal, lilial and bourgeonal, the ketones include, for example, the ionones, alpha-isomethylionone and methyl cedryl ketone, the alcohols include anethol, citronellol, eugenol, geraniol, linalol, phenylethyl alcohol and terpineol; and the hydrocarbons include primarily the terpenes and balsams. Preference is given to using mixtures of different odorants which together produce a pleasing scent note.

Perfume oils may also comprise natural odorant mixtures, as are accessible from vegetable or animal sources, e.g. pine oil, citrus oil, jasmine oil, lily oil, rose oil or ylang-ylang oil. Essential oils of relatively low volatility, which in most cases are used as aromatic components, are also suitable as perfume oils, e.g. sage oil, chamomile oil, clove oil, melissa oil, mint oil, cinnamon leaf oil, linden blossom oil, juniper berry oil, vetiver oil, olibanum oil, galbanum oil and ladanum oil.

Suitable for use as opacifiers are polymer dispersions, in particular polyacrylate derivative, polyacrylamide derivative, poly(acrylate derivative-co-acrylamide derivative) dispersions, poly(styrene derivative-co-acrylate derivative) dispersions, saturated and unsaturated fatty alcohols.

The substances mentioned above under silicone oils and waxes may be used as silicones.

Mineral acids, in particular HCl, inorganic bases, in particular NaOH or KOH, and organic acids, in particular citric acid, may preferably be used as acids or bases for adjusting the pH.

The cosmetic, dermatological or pharmaceutical compositions according to the invention have a pH of preferably from 2 to 11 and particularly preferably from 4.5 to 8.5 and especially preferably from 2.5 to 6.5.

In an advantageous manner, mixtures of one or more compounds of the formula (I) and one or more substances selected from the group consisting of hydroxypyridones and their salts or of premixes according to the invention are suitable for preserving cosmetic, dermatological or pharmaceutical compositions.

Accordingly, the present invention furthermore provides the use of one or more compounds of the formula (I) and one or more substances selected from the group consisting of hydroxypyridones and their salts or of premixes according to the invention for preserving cosmetic, dermatological or pharmaceutical compositions. Here, the cosmetic, dermatological or pharmaceutical compositions are preferably preserved against bacteria, yeasts and fungi. In a particularly preferred embodiment of the invention, the cosmetic, dermatological or pharmaceutical compositions are preserved against bacteria. In a further particularly preferred embodiment of the invention, the cosmetic, dermatological or pharmaceutical compositions are preserved against yeasts. In a further particularly preferred embodiment of the invention, the cosmetic, dermatological or pharmaceutical compositions are preserved against fungi.

The examples and applications which follow are intended to illustrate the invention in more detail, without, however, limiting it. All percentages are % by weight, unless explicitly stated otherwise.

EXPERIMENTAL EXAMPLES

A) Preparation of Isosorbide Caprylate

In a stirred apparatus with distillation head, 190.0 g (1.3 mol) of isosorbide ("Sorbon" from Ecogreen Oleochemicals) and 187.5 g (1.3 mol) of octanoic acid (caprylic acid) are initially charged at 80° C. together with 0.38 g of aqueous sodium hydroxide solution (18% by weight strength, aqueous) as catalyst. With stirring and under a flow of nitrogen (10-12 liters per hour), the reaction mixture is initially heated to 180° C., where the water of reaction begins to distill off. The reaction is then heated to 190° C. over a period of 1 hour and to 210° C. over a further 2 hours. After 210° C. is reached, the esterification is continued until an acid value of <1 mg KOH/g is reached. This gives 345.7 g of amber isosorbide caprylate (97% of theory). The pH (5% by weight in ethanol/water 1:1) is 5.9. The pH was measured according to DIN EN 1262.

Further analytical characteristics of the isosorbide caprylate:
Acid value: 0.9 mg KOH/g, measured according to DIN EN ISO 2114
Hydroxy value: 206 mg KOH/g, measured analogously to DIN 53240-2 according to method OHV-A
Saponification value: 204 mg KOH/g, measured according to DIN EN ISO 3681

The isosorbide caprylate has the following composition:

| Substance | % by weight |
| --- | --- |
| caprylic acid | 0.4 |
| isosorbide | 18.1 |
| isosorbide monocaprylate | 50.9 |
| isosorbide dicaprylate | 30.6 |

Hereinbelow, this composition is referred to as "isosorbide caprylate 1"

B) Determination of the Antimicrobial Efficacy of the Compositions According to the Invention Below, the antimicrobial efficacy of a composition according to the invention consisting of 50% by weight of isorbide caprylate 1 and 50% by weight of a 10% by weight strength solution of the monoethanolamine salt of 4-methyl-6-(2,4,4-trimethylpentyl)-1-hydroxy-2-pyridone (Octopirox®, 100% by weight strength, Clariant) in butyl polyglycol against bacteria, fungi and yeasts is examined (hereinbelow, the composition is referred to as "composition A"). For the tests with bacteria, composition A was diluted with butyl polyglycol and then, at 50° C., added to liquid CASO agar (casein-peptone agar) buffered to pH 7 (+/−0.2) in various concentrations (hereinbelow referred to as compositions B1, B2, etc.). For the tests with fungi and yeasts, composition A was diluted with butyl polyglycol and then added to liquid Sabouraud 4% dextrose agar buffered to pH 5.6 (+/−0.2) in various concentrations (hereinbelow referred to as compositions PH1, PH2, etc.). The compositions B1, B2, etc. and PH1, PH2 etc. were each poured into Petri dishes and each inoculated with identical amounts of bacteria, fungi and yeasts. The minimum inhibitory concentration (MIC) is the concentration at which inhibition of the growth of the bacteria, fungi and yeasts in the compositions B1, B2, etc. and PH1, PH2, etc. occurs.

The minimum inhibitory concentrations for the pure substances isosorbide caprylate 1 and Octopirox® were determined analogously.

The values determined for the minimum inhibitory concentrations "MIC mixture", stated in Table 1 below, are based on the concentrations of composition A.

The values determined for the minimum inhibitory concentrations "$Q_A$" and "$Q_B$", stated in Table 1 below, have already been corrected for the dilution effect of the butyl polyglycol.

From the minimum inhibitory concentrations determined, it is then possible to calculate whether a synergistic effect is present or not. Whether a synergistic effect is present is calculated according to F. C. Kull et al., Applied Microbiology 1961, 9, 538 using the formula below:

$$SE = Q_a/Q_A + Q_b/Q_B$$

where
$Q_a$ is the minimum inhibitory concentration of isosorbide caprylate 1 in the mixture employed,
$Q_A$ is the minimum inhibitory concentration of isosorbide caprylate 1,
$Q_b$ is the minimum inhibitory concentration of Octopirox® in the mixture employed and
$Q_B$ is the minimum inhibitory concentration of Octopirox®.

The values for $Q_a$ and $Q_b$ are determined from the values for the mixtures ("MIC mixture") by multiplying the minimum inhibitory concentrations determined for $Q_a$ with the factor 0.5 and for $Q_b$ with the factor 0.05, because of the proportions of the ingredients—50% by weight of isosorbide caprylate 1 and 50% by weight of a 10% by weight strength solution of Octopirox® in butyl polyglycol—in composition A according to the invention examined.

If an SE value>1 is obtained, an antagonistic effect is present. If SE=1, the compounds are neutral with respect to one another, and if SE<1, a synergistic effect is present.

The results of the examination of composition A are stated in Table 1 below.

TABLE 1

Results of the examination of the antimicrobial efficacy of composition A

| Bacteria, fungi or yeasts examined | MIC mixture, meas. [ppm] | $Q_a$, calc. [ppm] | $Q_A$, meas. [ppm] | $O_b$, calc. [ppm] | $O_B$, meas. [ppm] | SE |
| --- | --- | --- | --- | --- | --- | --- |
| Staphylococcus aureus | 500 | 250 | 2500 | 25 | 25 | 1.1 |
| Pseudomonas aeruginosa | 500 | 250 | 10000 | 25 | 25 | 1.025 |
| Escherichia coli | 500 | 250 | 7500 | 25 | 25 | 1.03 |
| Enterobacter aerogenes | 500 | 250 | 10000 | 25 | 100 | 0.275 |
| Klebsiella pneumoniae | 500 | 250 | 10000 | 25 | 50 | 0.525 |
| Proteus vulgaris | 250 | 125 | 5000 | 12.5 | 25 | 0.525 |
| Pseudomonas oleovorans | 500 | 250 | 10000 | 25 | 50 | 0.525 |
| Citrobacter freundii | 500 | 250 | 10000 | 25 | 50 | 0.525 |
| Candida albicans | 200 | 100 | 600 | 10 | 20 | 0.66 |
| Aspergillus brasiliensis | 200 | 100 | 800 | 10 | 20 | 0.625 |
| Penicillium minioluteum | 200 | 100 | 600 | 10 | 20 | 0.66 |
| Aspergillus terreus | 200 | 100 | 600 | 10 | 20 | 0.66 |
| Fusarium solani | 200 | 100 | 600 | 10 | 20 | 0.66 |
| Penicillium funicolosium | 200 | 100 | 400 | 10 | 20 | 0.75 | meas.: measured; calc.: calculated

The results listed in Table 1 show that a composition according to the invention consisting of 50% by weight of isosorbide caprylate 1 and 50% by weight of a 10% by weight solution of the monoethanolamine salt of 4-methyl-6-(2,4,4-trimethylpentyl)-1-hydroxy-2-pyridone (Octopirox®, Clariant) in butyl polyglycol for all tested bacteria (apart from *Staphylococcus aureus*, *Pseudomonas aeruginosa* and *Escherichia coli*), fungi and yeasts has a synergistic effect with respect to their antimicrobial activity.

C) Antimicrobial Activity of the Constituents of Isosorbide Caprylate 1

Caprylic acid is antimicrobially effective. However, since in the composition "isosorbide caprylate 1" caprylic acid is present in an amount of only 0.4% by weight, its antimicrobial efficacy in this composition is so low that it is negligible. In addition, caprylic acid has no antimicrobial activity at a pH of 6 or above.

Analogously to the determination of the antimicrobial activity according to the above example B), the antimicrobial activity of a mixture comprising, firstly, 89.6% by weight of isosorbide dicaprylate and 9.4% by weight of isosorbide monocaprylate (remainder: 1% by weight) (hereinbelow referred to as "isosorbide dicaprylate") and, secondly, pure isosorbide was determined in further test series. The results are shown in Table 2.

TABLE 2

Minimum inhibitory concentrations (MICs) of isosorbide dicaprylate and isosorbide

| Bacteria (B), fungi (F) or yeasts (Y) examined | MIC of isosorbide dicaprylate [ppm] | MIC of isosorbide [ppm] |
|---|---|---|
| *Staphylococcus aureus* (B) | 10000 | 10000 |
| *Pseudomonas aeruginosa* (B) | 10000 | 10000 |
| *Escherichia coli* (B) | 10000 | 10000 |
| *Enterobacter aerogenes* (B) | 10000 | 10000 |
| *Klebsiella pneumoniae* (B) | 10000 | 10000 |
| *Proteus vulgaris* (B) | 10000 | 10000 |
| *Pseudomonas oleovorans* (B) | 10000 | 10000 |
| *Citrobacter freundii* (B) | 10000 | 10000 |
| *Candida albicans* (Y) | 10000 | 10000 |
| *Aspergillus brasiliensis* (F) | 10000 | 10000 |
| *Penicillium minioluteum* (F) | 10000 | 10000 |
| *Aspergillus terreus* (F) | 10000 | 10000 |
| *Fusarium solani* (F) | 5000 | 10000 |
| *Penicillium funicolosium* (F) | 5000 | 10000 |

As shown by the results of Table 2, neither isosorbide nor isosorbide dicaprylate are antimicrobially active.

From the lack of antimicrobial activity of the compounds caprylic acid, isosorbide and isosorbide dicaprylate present in the composition isosorbide caprylate 1 on the one hand and from the antimicrobial activity of the composition "isosorbide dicaprylate 1" evident from the results of table 1 on the other hand (see minimum inhibitory concentration $Q_A$ for isosorbide caprylate 1 in Table 1), it can be concluded that the compound isosorbide monocaprylate likewise present in the composition isosorbide caprylate 1 has significant antimicrobial activity.

For this reason, it is also thought that the low activity of the composition isosorbide dicaprylate with respect to the fungi *Fusarium solani* and *Penicillium funicolosium* is due to the compound isosorbide monocaprylate present therein.

D) Use Examples

I) Examples of the Compositions According to the Invention

Examples a)-d)

Compositions consisting of a) 90% by weight of isosorbide caprylate 1, 10% by weight of Octopirox® b) 95% by weight of isosorbide caprylate 1, 5% by weight of Octopirox® c) 80% by weight of isosorbide caprylate 1, 5% by weight of Octopirox®, 15% by weight of propylene glycol d) 70% by weight of isosorbide caprylate 1, 3% by weight of Octopirox®, 27% by weight of benzyl alcohol The compositions of examples a) to d) are prepared by successively mixing the individual components with stirring on a finger stirrer at stirring rates of 200-300 revolutions/minute, with an initial charge of liquid isosorbide caprylate 1 heated to 80° C.

II) Examples of Cosmetic Formulations According to the Invention

The following cosmetic formulations 1-28 are prepared using compositions according to the invention of examples a)-d):

Formulation Examples 1-4

Hair Care Gels for Strong Hold and Excellent Styling

| | Formulation No. | | | |
|---|---|---|---|---|
| | 1 | 2 | 3 | 4 |
| Ingredient | Amount of the respective ingredient [% by weight] | | | |
| Aristoflex ® AVC | 1.0 | 1.0 | 1.0 | 1.0 |
| water | ad 100 | ad 100 | ad 100 | ad 100 |
| carbomer | — | 0.5 | 0.5 | — |
| NaOH | — | q.s. | q.s. | — |
| PEG-40 hydrogenated castor oil | 1.0 | 1.0 | 1.0 | — |
| fragrance | 0.3 | 0.3 | — | 0.3 |
| ethanol (96% by weight in water) | 10.0 | 10.0 | 5.0 | — |
| Diaformer ® Z-712 N (acrylates/lauryl acrylate/stearyl acrylate/ethylamine oxide methacrylate) | 4.5 | 4.5 | — | 6.0 |
| Luviskol ® VA 64 (PVP/VA) | 3.0 | 3.0 | 5.0 | — |
| propylene glycol | 1.0 | 1.0 | — | 1.0 |
| panthenol | 0.5 | 0.5 | — | — |
| dyestuff solution | q.s. | q.s. | q.s. | — |
| Example a)-d) according to the invention | 0.8 | 0.8 | 0.5 | 0.7 |

Preparation:

Aristoflex® AVC is dissolved in water. If carbomer is added, the mixture is subsequently neutralized with NaOH to pH=7. The other components are optionally mixed with PEG-40 hydrogenated castor oil and stirred into the thickened aqueous phase.

Formulation Example 5

O/W Exfoliating Cream with High Electrolyte Content (Na Glycolate)

| Phase | Ingredient | % by weight |
|---|---|---|
| A | PEG-120 methyl glucose dioleate | 1.5 |
| B | water | ad 100 |
| C | mineral oil | 5.0 |
|   | caprylyl trimethicone | 3.0 |
| D | Aristoflex ® AVC | 1.2 |
| E | glycolic acid 30% by weight in water (neutralized with NaOH to pH = 4) | 6.0 |
|   | Example a)-d) according to the invention | 0.6 |
| F | laureth-7 | 3.0 |

Preparation:

A is dissolved with heating in phase B. Phase C is dispersed in phase D and stirred into the aqueous phase. Phases E and F are then stirred in.

Formulation Example 6

W/O Skin Care Milk

| Phase | Ingredient | % by weight |
|---|---|---|
| A | amodimethicone glycerocarbamate | 2.0 |
|   | cyclopentasiloxane | 5.0 |
|   | paraffin oil | 3.5 |
|   | apricot kernel oil | 1.0 |
|   | grape seed oil | 0.5 |
|   | microcrystalline wax | 0.7 |
|   | stearic acid | 0.5 |
|   | ethylhexyl cocoate | 7.0 |
| B | Aristoflex ® AVC | 0.3 |
| C | water | ad 100 |
|   | glycerol | 3.5 |
|   | Example a)-d) according to the invention | 0.5 |

Preparation:

Oil phase A is heated to 80° C. and polymer B is stirred in. Phase C is added slowly in small portions with vigorous stirring, and the mixture is allowed to cool to room temperature.

Formulation Example 7

Makeup Remover with Excellent Skin Feel

| Phase | Ingredient | % by weight |
|---|---|---|
| A | isopropyl C$_{12-15}$ pareth-9 carboxylate | 5.0 |
| B | sodium cocoyl glutamate (25% by weight strength solution in water) | 2.3 |
|   | cocamidopropyl betaine (30% by weight strength solution in water) | 3.0 |

| Phase | Ingredient | % by weight |
|---|---|---|
|   | laureth-7 | 2.0 |
|   | water | ad 100 |
|   | allantoin | 0.3 |
|   | polypropylene terephthalate | 1.0 |
|   | 1,6-hexanediol | 2.0 |
|   | propylene glycol | 2.0 |
|   | PEG-8 | 2.0 |
|   | panthenol | 0.5 |
|   | poloxamer 407 | 3.0 |
|   | Example a)-d) according to the invention | 0.8 |
|   | Aristoflex ® HMB | 1.0 |

Preparation:

The components of B are dissolved successively in A.

Formulation Example 8

Shampoo/Shower Gel with Suspended Particles

| Phase | Ingredient | % by weight |
|---|---|---|
| A | water | ad 100 |
| B | Aristoflex ® TAC | 2.0 |
| C | sodium laureth sulfate (30% by weight in water) | 18.5 |
|   | perfume | 0.5 |
|   | Example a)-d) according to the invention | 0.4 |
| D | sodium cocoyl glutamate (25% by weight strength solution in water) | 20.0 |
| E | synthetic wax | 0.2 |

Preparation:

Aristoflex® TAC is dissolved in water, phases C, D and E are then introduced successively and the mixture is homogenized.

Formulation Example 9

Clear Deodorizing Gel

| Phase | Ingredient | % by weight |
|---|---|---|
| A | PEG-40 (hydrogenated castor oil | 1.0 |
|   | perfume | 0.1 |
| B | ethanol (96% by weight in water) | 25.0 |
|   | Example a)-d) according to the invention | 0.4 |
| C | propylene glycol | 20.0 |
|   | diisopropyl adipate | 1.0 |
|   | water | ad 100 |
| D | Aristoflex ® AVC | 1.3 |
| E | citric acid | q.s. |

Preparation:

Phase A is mixed, phase B and phase C are then added in succession and the pH is adjusted to 5.5 using phase E. Phase D is then stirred in until a homogenous clear gel is formed.

Formulation Example 10

Mattifying Serum

| Phase | Ingredient | % by weight |
|---|---|---|
| A | water | ad 100 |
| B | glycerol | 3.0 |
|  | Aristoflex ® HMB | 0.5 |
|  | caprylyl methicone | 1.5 |
|  | cyclomethicone and dimethicone crosspolymer (Dow Corning 9040 silicone elastomer blend) | 1.0 |
|  | fragrance | 0.15 |
|  | Example a)-d) according to the invention | 0.4 |

Preparation:

The components of B are stirred in successively into phase A.

Formulation Example 11

Skin Whitening Gel

| Phase | Ingredient | % by weight |
|---|---|---|
| A | allantoin | 0.5 |
| B | water | ad 100 |
| C | xanthan gum | 0.5 |
| D | ascorbic acid 2-glucoside | 2.0 |
| E | NaOH (25% by weight strength solution in water) | q.s. |
| F | glycerol | 10.0 |
|  | ethanol (96% by weight in water) | 10.0 |
|  | PEG/PPG-18/18 dimethicone (Dow Corning ® 190, Dow Corning) | 1.0 |
|  | PEG-40 hydrogenated castor oil | 0.8 |
| G | Aristoflex ® AVS | 1.0 |
| H | NaOH (25% by weight strength solution in water) | q.s. |
| I | Example a)-d) according to the invention | 0.6 |

Preparation:

Phase A is dissolved in phase B with heating, phase C is stirred in, phase D is added and the pH is adjusted to 6.5 using phase E. Phase F is mixed and then added, phase G is then added and the mixture is stirred until a homogeneous gel is obtained. If appropriate, the pH is adjusted to 6.5 using phase H, and phase I is stirred in.

Formulation Example 12

Elegant O/W Skin Care Body Lotion with Low Tackiness

| Phase | Ingredient | % by weight |
|---|---|---|
| A | caprylic/capric triglyceride | 3.5 |
|  | myristyl myristate | 2.5 |
|  | cetearyl alcohol | 2.0 |
|  | glyceryl stearate citrate | 1.0 |
|  | octyldodecanol | 1.0 |
| B | Aristoflex ® AVC | 0.6 |
| C | water | ad 100 |
|  | glycerol | 7.5 |
| D | ethanol (96% by weight in water) | 3.0 |
|  | dimethicone | 3.0 |
|  | tocopheryl acetate | 1.0 |
|  | *Aloe barbadensis* | 1.0 |
|  | Example a)-d) according to the invention | 0.7 |
|  | fragrance | q.s. |
| E | NaOH (10% by weight in water) | q.s. |

Preparation:

Phase A is melted at 70° C., phase B is poured in and phase C, heated to 70° C., is stirred in. After cooling to 35° C., phase D is stirred in and the pH is then adjusted to 6 using phase E.

Formulation Example 13

Surfactant-Free Anti-Aging O/W Gel Cream with Wrinkle-Reducing Action

| Phase | Ingredient | % by weight |
|---|---|---|
| A | dicaprylyl ether | 5.0 |
|  | caprylic/capric triglyceride | 5.0 |
|  | cetearyl alcohol | 2.0 |
|  | Example a)-d) according to the invention | 0.6 |
| B | ubiquinone | 0.1 |
| C | Aristoflex ® HMB | 1.1 |
| D | sodium hyaluronate (Dekluron) | 0.3 |
|  | glycerol | 8.0 |
| E | water | ad 100 |
|  | mica and titanium dioxide and tin oxide (Prestige ® Soft Orange, Eckart) | 0.5 |
| F | tocopheryl acetate | 0.3 |
| G | NaOH (10% by weight in water) | q.s. |

Preparation:

Phase A is melted at 80° C., phase B and phase C are stirred in successively. Phase D is pre-dissolved in phase E and added. Phase F is stirred in at 35° C., and the pH is adjusted to 6.0 using phase G. A gel cream is formed.

Formulation Example 14

Surfactant-Free Anti-Aging O/W Gel Cream

| Phase | Ingredient | % by weight |
|---|---|---|
| A | dicaprylyl ether | 5.0 |
|  | caprylic/capric triglyceride | 5.0 |
|  | cetearyl alcohol | 2.0 |
|  | Example a)-d) according to the invention | 0.8 |
| B | ubiquinone | 0.1 |
| C | Aristoflex ® HMB | 1.1 |
| D | xanthan gum | 0.2 |
|  | glycerol | 8.0 |
| E | water | ad 100 |
|  | mica and titanium dioxide and tin oxide (Prestige ® Soft Orange, Eckart) | 0.5 |

| Phase | Ingredient | % by weight |
|---|---|---|
| F | tocopheryl acetate | 0.3 |
| G | NaOH (10% by weight in water) | q.s. |

Preparation:

Phase A is melted at 80° C., phase B and phase C are stirred in successively. Phase D is pre-dissolved in phase E and added. Phase F is stirred in at 35° C., and the pH is adjusted to 6.0 using phase G. A gel cream is formed.

Formulation Example 15

O/W Self-Tanning Cream with Moisturizing Effect

| Phase | Ingredient | % by weight |
|---|---|---|
| A | cetyl phosphate | 1.0 |
| | glyceryl stearate | 0.5 |
| | cetearyl alcohol | 0.5 |
| | isohexadecane | 8.0 |
| | isopropyl palmitate | 7.0 |
| | caprylyl methicone | 1.0 |
| B | Aristoflex ® AVS | 1.0 |
| C | water | ad 100 |
| | sodium cocoyl glutamate | 0.5 |
| | glycerol | 5.0 |
| | NaOH (10% by weight in water) | 0.5 |
| D | tocopheryl acetate | 1.0 |
| | fragrance | 0.2 |
| | Example a)-d) according to the invention | 0.5 |
| E | dihydroxyacetone | 5.0 |
| | water | 8.0 |

Preparation:

Phase A is melted at 80° C., phase B and phase C are stirred in successively. Phase D is added at 30° C. and finally phase E is stirred in. This results in a cream having a pH of 4.2.

Formulation Examples 16-21

W/O Sun Protection Formulations with High Protection Factor

| | Formulation No. | | | | | |
|---|---|---|---|---|---|---|
| | 16 | 17 | 18 | 19 | 20 | 21 |
| Ingredient | Amount of the respective ingredient [% by weight] | | | | | |
| C$_{12-15}$ alkyl benzoate | 8.0 | 8.0 | 8.0 | 8.0 | 8.0 | 8.0 |
| caprylic/capric triglyceride | 5.0 | 5.0 | 5.0 | 5.0 | 5.0 | 5.0 |
| octocrylene | 9.0 | — | 5.0 | 4.0 | — | — |
| ethylhexyl methoxycinnamate | 7.0 | 7.0 | 7.0 | — | 6.0 | 6.0 |
| butyl methoxydibenzoylmethane | 2.5 | — | 2.5 | — | — | — |
| disodium phenyl dibenzimidazole tetrasulfonate | — | — | — | — | — | 3.0 |
| ethylhexyl bisisopentylbenzoxazolylphenylmelamine | — | — | — | — | 2.0 | — |
| diethylamino hydroxybenzoyl hexyl benzoate | — | — | 2.0 | 1.0 | — | — |
| bis-ethylhexyloxyphenol methoxyphenyl triazine | — | 3.0 | — | 2.0 | 4.0 | 3.0 |
| methylene bisbenzotriazolyl tetramethylbutylphenol | — | 3.0 | — | — | — | 2.0 |
| ethylhexyl triazone | — | — | — | 3.0 | — | — |
| diethylhexyl butamido triazone | — | — | — | — | 2.0 | — |
| polysilicone-15 | — | — | 2.0 | — | — | — |
| phenylbenzimidazole sulfonic acid | — | — | — | 3.0 | — | — |
| titanium dioxide | — | 5.0 | 3.0 | 4.0 | 5.0 | 5.0 |
| cetearyl alcohol | 1.0 | 1.0 | 1.0 | 1.0 | 1.0 | 1.0 |
| sunflower seed oil sorbitol esters | 2.0 | 2.0 | 2.0 | 2.0 | 2.0 | 2.0 |
| Example a)-d) according to the invention | 0.8 | 0.8 | 0.8 | 0.8 | 0.8 | 0.8 |
| potassium cetylphosphate | 3.0 | 3.0 | 3.0 | 3.0 | 3.0 | 3.0 |
| Aristoflex ® AVC | 1.0 | 0.6 | 0.5 | 0.9 | 1.0 | 1.0 |
| water | ad 100 | ad 100 | ad 100 | ad 100 | ad 100 | ad 100 |
| nylon | — | 0.5 | — | — | — | — |
| bisethyl hexyl hydroxy-dimethoxy benzylmalonate | — | — | 1.0 | — | — | — |
| talc | — | — | — | — | 0.5 | — |

Preparation:

For the preparation, the oil-soluble components were heated to 80° C., potassium cetylphosphate and Aristoflex® AVC were poured in and the combined water-soluble phases were slowly, with vigorous stirring, introduced into the oil phase. The emulsions formed were allowed to cool to room temperature while stirring.

The sun protection filters used in formulation examples 16-21, their tradenames and their UV protection range are listed in the table below.

| Sun protection filter | Trade name | Protection range (UV-A/UV-B) |
|---|---|---|
| octocrylene | Neo Heliopan ® 303 | B |
| ethylhexyl methoxycinnamate | Neo Heliopan ® AV | B |
| butyl methoxydibenzoylmethane | Neo Heliopan ® 357, Parsol ® 1789 | A |
| disodium phenyl dibenzimidazole tetrasulfonate | Neo Heliopan ® AP | A |
| ethylhexyl bisisopentylbenzoxazolylphenyl-melamine | Uvasorb ® K2A | A |
| diethylamino hydroxybenzoyl hexyl benzoate | Uvinul ® A Plus | A |
| bis-ethylhexyloxyphenol methoxyphenyl triazine | Tinosorb ® S | A/B |
| methylene bisbenzotriazolyl tetramethylbutylphenol | Tinosorb ® M | A/B |
| ethylhexyl triazone | Uvinul ® T 150 | B |
| diethylhexyl butamido triazone | Uvasorb ® HEB | B |
| polysilicone-15 | Parsol ® SLX | B |
| phenylbenzimidazole sulfonic acid | | B |

Formulation Example 22

O/W Sun Protection Cream

| Phase | Ingredient | % by weight |
|---|---|---|
| A | ethylhexyl methoxycinnamate | 6.0 |
| | ethylhexyltriazone | 2.0 |

| Phase | Ingredient | % by weight |
|---|---|---|
|  | benzophenone-3 | 2.0 |
|  | BHT | 0.05 |
| B | Aristoflex ® AVS | 1.5 |
|  | trilaureth-4 phosphate | 2.0 |
|  | polyglyceryl-2 sesquiisostearate | 1.0 |
|  | caprylyl methicone | 1.0 |
|  | Example a)-d) according to the invention | 0.7 |
|  | PVP/hexadecene copolymer | 1.0 |
|  | tocopheryl acetate | 0.5 |
|  | fragrance | 0.2 |
| C | water | ad 100 |
|  | disodium EDTA | 0.1 |
| D | methylene bisbenzotriazolyl tetramethylbutylphenol | 4.0 |
| E | triethanolamine | q.s. |

Preparation:

Phase A is homogenized and dissolved at 60° C. and stirred into phase B, phase C is then added with stirring and the mixture is stirred at 300 revolutions per minute. Phase D is then stirred in, and the pH is adjusted to 6.8-7.2 using E.

Formulation Example 23

Sprayable O/W Lotion

| Phase | Ingredient | % by weight |
|---|---|---|
| A | trilaureth-4 phosphate | 1.0 |
|  | mineral oil | 8.0 |
|  | isopropyl palmitate | 3.0 |
|  | cetearyl alcohol | 0.5 |
|  | caprylic/capric triglyceride | 2.0 |
|  | glyceryl stearate | 0.5 |
|  | caprylyl methicone | 1.0 |
| B | Aristoflex ® AVC | 0.2 |
| C | water | ad 100 |
|  | glycerol | 5.0 |
| D | fragrance | 0.3 |
|  | ethanol (96% by weight in water) | 5.0 |
| E | Example a)-d) according to the invention | 0.6 |

Preparation:

Phase A is heated to 60° C., phase B is stirred in, phase C is then added with stirring and the mixture is stirred at 300 revolutions per minute and allowed to cool. Phase D is stirred in at 35° C., phase E is added and the mixture is then homogenized.

Formulation Example 24

O/W Foundation

| Phase | Ingredient | % by weight |
|---|---|---|
| A | hydrogenated polydecene | 9.0 |
|  | caprylic/capric triglyceride | 5.0 |
|  | caprylyl trimethicone | 4.0 |
|  | caprylyl methicone | 3.0 |
|  | steareth-2 | 1.6 |
|  | steareth-20 | 2.4 |
|  | Aristoflex ® HMB | 0.4 |
| B | kaolin | 1.5 |
|  | talc | 3.0 |
|  | iron oxide | 7.9 |
| C | glycerol | 5.0 |
|  | water | ad 100 |
| D | Example a)-d) according to the invention | 0.6 |
|  | fragrance | q.s. |

Preparation:

Phase A is heated to 70° C., phase C is heated to 70° C. Phase B is stirred into phase A, phase C is then added and the mixture is thoroughly homogenized. After cooling to below 40° C., phase D is added and the mixture is homogenized for one minute.

Formulation Example 25

Anti-Dandruff Shampoo

| Phase | Ingredient | % by weight |
|---|---|---|
| A | Example a)-d) according to the invention | 1.0 |
| B | water | 10.0 |
| C | sodium laureth sulfate | 30.0 |
| D | climbazole | 0.5 |
| E | 1,2-propylene glycol | 2.0 |
| F | sodium cocoyl glutamate | 4.0 |
|  | fragrance | 0.3 |
|  | water | ad 100 |
|  | Merquat ® 550 polyquaternium 7 | 0.5 |
|  | panthenol | 0.5 |
|  | sodium salicylate | 1.0 |
|  | Genagen ® KB (Clariant) coco betaine | 8.0 |
|  | dyestuff solution | q.s. |
| G | sodium chloride | 1.0 |

Preparation:
I A is mixed with B.
II C is added to I and the mixture is stirred, until a clear solution is obtained.
III D is dissolved in E and the solution is added to II.
IV The components of F are successively stirred into III.
V The pH is adjusted to 6.0-6.5.
VI The viscosity is adjusted using G.

Formulation Example 26

Anti-Acne Face Cleanser

| Phase | Ingredient | % by weight |
|---|---|---|
| A | Genagen ® CAB (Clariant) cocamidopropyl betaine | 10.0 |
| B | fragrance | 0.2 |
|  | Hostapon ® CLG (Clariant) cocoyl lauroyl glutamate | 2.0 |
|  | Hostapon ® CT Paste (Clariant) sodium methyl cocoyl taurate | 2.0 |
|  | glycerol | 1.0 |
|  | Aristoflex ® PEA (Clariant) | 1.0 |

-continued

| Phase | Ingredient | % by weight |
|---|---|---|
| | polypropylene terephthalate Cetiol ® HE (Cognis) | 1.0 |
| | Example a)-d) according to the invention | 1.0 |
| | *Aloe vera* gel conc. Water (and) *Aloe barbadensis* gel | 1.0 |
| | Extrapone camomile water (and) ethoxydiglycol (and) propylene glycol (and) *Matricaria* extract (and) butylene glycol (and) glycose (and) bisabolol | 1.0 |
| | water | ad 100 |
| | D-panthenol | 0.5 |
| C | citric acid | q.s. |

Preparation:
I A is initially charged and the components of B are added successively with stirring.
II The pH is adjusted to 5.5-6.0 using C.

Formulation Example 27

Scalp Gel

| Phase | Ingredient | % by weight |
|---|---|---|
| A | Promyristyl ® PM-3 PPG-3 myristyl ether | 6.0 |
| | Lamesoft ® PO 65 coco-glucoside (and) glyceryl oleate | 3.0 |
| | Cetiol ® SB 45 *Butyrospermum parkii* (shea butter) | 2.0 |
| B | water | ad 100 |
| | glycerol | 4.0 |
| | sodium salicylate | 2.0 |
| | allantoin (Clariant) allantoin | 0.4 |
| | Merquat 2001 polyquaternium-47 | 0.5 |
| C | urea | 10.0 |
| D | Aristoflex ® AVC (Clariant) ammonium acryloyldimethyltaurate/VP copolymer | 1.8 |
| E | Example a)-d) according to the invention | 0.6 |
| F | lactic acid | q.s. |

Preparation
I The components of A are mixed and dissolved at 50° C.
II The components of B are mixed with stirring and gentle heating.
III C is dissolved at about 25° C. in II.
IV D is added to I.
V III is stirred into IV.
VI E is added.
VII The pH is adjusted to 5.0 using F.

Formulation Example 28

Solution for Wet Wipe

| Phase | Ingredient | % by weight |
|---|---|---|
| A | propylene glycol | 3.0 |
| | Example a)-d) according to the invention | 0.8 |
| B | water | ad 100 |
| | Genagen ® KB coco-betaine | 3.0 |
| | Genamin ® PQ43 polyquaternium-43 | 0.7 |
| | Aristoflex ® AVC ammonium acryloyldimethyltaurate/VP copolymer | 0.1 |
| C | citric acid | q.s. |

I The components of A are mixed.
II The components of B are mixed.
III II is added to I.
IV The pH is adjusted to pH 6.0 using C.

The statement "example a)-d) according to the invention" used in formulation examples 1-28 means that each of the formulation examples 1-28 can be prepared using any one of the compositions according to examples a)-d) according to the invention.

The invention claimed is:

1. A composition comprising a) one or more compounds of the formula (I)

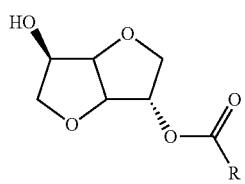

in which the radical R in formula (I) is a straight-chain saturated alkyl radical having 7 carbon atoms, and b) the compound of component b) is the monoethanolamine salt of 4-methyl-6-(2,4,4-trimethylpentyl)-1-hydroxy-2-pyridone, and the composition comprises, in addition to the one or more compounds of the formula (I), one or more compounds selected from the group consisting of sorbitol, sorbitol esters, sorbitan, sorbitan esters, isosorbide, isosorbide diesters and carboxylic acids, where the carboxylic acids themselves and the carboxylic acids on which the acid components of the esters mentioned are based correspond to the formula RCOOH in which R has the meaning given for formula (I), and the hydroxyl value of the mixture of the one or more compounds of the formula (I) and the one or more compounds selected from the group consisting of sorbitol, sorbitol esters, sorbitan, sorbitan esters, isosorbide, isosorbide diesters and carboxylic acids is smaller than or equal to 245.

2. The composition as claimed in claim 1, which comprises

I) from 0.05 to 0.7 part by weight of isosorbide and

II) from 0.1 to 1.0 part by weight of isosorbide diester of the formula

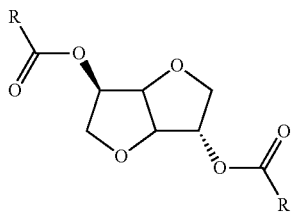

in which R has the meaning given for formula (I), and wherein the isosorbide diester is,
in each case based on 1.0 part by weight of the one or more compounds of the formula (I).

3. The composition as claimed in claim 1, which additionally comprises one or more sorbitan esters of sorbitan and carboxylic acids $R^aCOOH$, where $R^a$ is a straight-chain or branched saturated alkyl group having 5 to 11 carbon atoms or a straight-chain or branched mono- or polyunsaturated alkenyl group having 5 to 11 carbon atoms, and the weight ratio of the one or more compounds of the formula (I) to the one or more sorbitan esters just mentioned is from 70:30 to 100:0.

4. The composition as claimed in claim 3, wherein the one or more sorbitan esters of sorbitan and carboxylic acids $R^aCOOH$ are selected from sorbitan esters of sorbitan and caprylic acid.

5. The composition as claimed in claim 1, which comprises the one or more compounds of component a) in amounts of from 10.0 to 99.5% by weight and the one or more substances of component b) in amounts of from 0.5 to 50.0% by weight, in each case based on the total weight of the composition.

6. The composition as claimed in claim 1, which comprises the one or more compounds of component a) in amounts of from 0.01 to 10.0% by weight and the one or more substances of component b) in amounts of from 0.001 to 1.0% by weight, in each case based on the total weight of the composition.

7. The composition as claimed in claim 1, wherein it is formulated on an aqueous or aqueous-alcoholic basis or is present as an emulsion.

8. The composition as claimed in claim 1, wherein it has a pH of from 2 to 11.

9. A method of preserving a cosmetic, dermatological or pharmaceutical composition comprising adding one or more compounds of the formula (I) as claimed in claim 1 and one or more substances selected from the group consisting of hydroxypyridones and their salts or of a composition as claimed in claim 5 for preserving a cosmetic, dermatological or pharmaceutical composition.

10. The method of claim 9, wherein the cosmetic, dermatological or pharmaceutical composition is preserved against bacteria, yeasts and fungi.

* * * * *